United States Patent [19]

Heinz

[11] Patent Number: 4,847,206

[45] Date of Patent: Jul. 11, 1989

[54] METHOD FOR THE CRYSTAL MORPHOLOGICAL ANALYSIS OF BLOOD AND URINE, FOR EARLY DIAGNOSIS AND FOR THE PRODUCTION OF MEDICAMENTS

[75] Inventor: Ullrich Heinz, Rottweil, Fed. Rep. of Germany

[73] Assignee: Heinz Spagyrik Institut Ag, Switzerland

[21] Appl. No.: 99,342

[22] Filed: Sep. 18, 1987

[30] Foreign Application Priority Data

Jul. 28, 1987 [DE] Fed. Rep. of Germany ....... 3724988

[51] Int. Cl.$^4$ ............................................. G01N 33/48
[52] U.S. Cl. ..................... 436/63; 436/175; 436/177; 436/181; 436/811
[58] Field of Search ................. 436/63, 183, 164, 174, 436/175, 177, 178, 179, 181, 811, 2, 108, 4

[56] References Cited

U.S. PATENT DOCUMENTS

| | | | |
|---|---|---|---|
| 4,025,307 | 5/1977 | Randolph | 436/4 |
| 4,469,452 | 9/1984 | Sharpless | 436/2 |
| 4,554,132 | 11/1985 | Collins | 436/178 |
| 4,661,913 | 4/1987 | Wu | 436/63 |

FOREIGN PATENT DOCUMENTS 825906 7/1949 Fed. Rep. of Germany.

Primary Examiner—Kenneth M. Schor
Attorney, Agent, or Firm—Scully, Scott, Murphy & Presser

[57] ABSTRACT

This invention relates to a method for the crystal morphological analysis of blood and urine for early diagnosis of disease conditions in humans and animals and for the production of medicaments therefor.

11 Claims, 26 Drawing Sheets

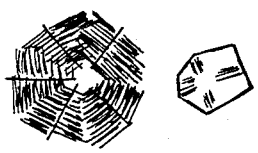
FIG.12

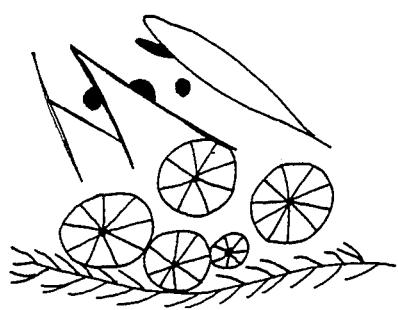
FIG.16  FIG.17
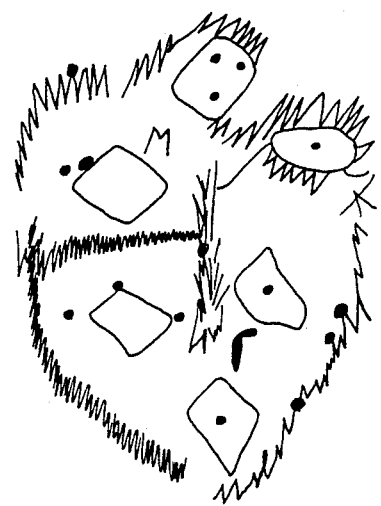
FIG.18

ENTODERM

HEAD CAVITIES
TEETH
PHARYNX / TONSILS
LYMPH
LUNGS
STOMACH / DUODENUM
SMALL INTESTINE
LARGE INTESTINE
RECTUM
LIVER
BLADDER
UTERUS / PROSTATE

MESODERM

PANCREAS
CONNECTIVE TISSUE
MUSCULATURE
BONES
JOINTS
KIDNEYS
HEART

ECTODERM

ENDOCRINE SYSTEM
SKIN
CENTRAL /
PERIPHERAL
NERVOUS SYSTEM

FIG. 19

METHOD FOR THE CRYSTAL MORPHOLOGICAL ANALYSIS OF BLOOD AND URINE, FOR EARLY DIAGNOSIS AND FOR THE PRODUCTION OF MEDICAMENTS

BACKGROUND OF THE INVENTION

The subject invention relates to crystal morphological analysis of blood and urine for early diagnosis and for the production of medicaments. Diagnostic methods presently in use include radiological; serological, sonographic and enzymatic methods.

SUMMARY OF THE INVENTION

The subject invention provides highly sensitive and highly specific forms of diagnosis for the representation as a whole of the pathological and physiological processes in the human and animal body as early diagnosis of the smallest changes, which in this stage can not yet be established by radiological, serological, sonographic, or enzymatic methods.

The crystal morphological analysis of blood or urine is accomplished by the following method:

1. distilling a mixture of blood or urine, preferably 3 to 15 ml, most preferably 7 to 10 ml, of a warm-blooded animal with distilled water said mixture being in a volume ratio of blood or urine to water of 1:2.5 to 3.5, preferably of 1:27 to 3.2, to provide a distillate and a dry cake of blood or urine sediment (preferably the distilled water is triple distilled);
2. calcining the dry cake of blood or urine sediment by heating at a constant rate for a period of 60 to 70 min., preferably 65 min., to a temperature of about 600° C. to provide a calcinate;
3. cooling the calcinate down to approximately 150° C. in approximately 2 to 4 hours;
4. pulverizing the cooled calcinate;
5. mixing the distillate from step 1 with the pulverized calcinate;
6. maintaining the mixture of step 5 under quiescent conditions for a period of 8 to 16 hours to provide a homogeneous fluid mixture;
7. filtering the homogeneous fluid mixture;
8. forming crystals from the filtered mixture on glass microscope slides by applying drops with a diameter of 6 to 10 mm, preferably 8 mm, of the filtered mixture on the glass slides under conditions of relative humidity of approximately 40 to 60% and a temperature of about 20° C., preferably 20° C., and evaporating the water from the drops at a temperature of about 20° C. to provide on the glass slide crystals with an outer concentric annulus designated the endodermal region (A) of FIG. 19, a middle concentric annulus designated the mesodermal region (B) of FIG. 19, and a central annulus designated the ectodermal region (C) of FIG. 19;
9. microscopically analyzing the form and texture of the crystals in the microscopic dark field with
   (a) an enlargement of 10 to 15 times to show the regions overall,
   (b) an enlargement of 20 to 50 times to show the individual form and texture of regions (A), (B), and (C),
   (c) an enlargement of 60 to 160 times to show the form and texture of compact, areal and/or spatial dendrites; and
   (d) an enlargement of 170 to 800 times to show the dendrite images with morphological, geometric, spatial basic forms for the identication of the crystal-forming basic forms; and
10. comparing the microscopic analysis of step (9) with a series of established pathological microscopic standards or with the coordinates of mother- and daughter forms to provide a diagnosis of the condition of health or disease of the human, vertebrate or mammal.

In another aspect of the invention, the distillate from step 1 may be used as auto-vaccine, or an anti-vaccine may be produced through multiplication of the microorganisms contained in the blood or urine on a blood agar base at 35° C. to 40° C. incubation temperature after removal and treatment according to steps 1 to 7, thereby providing a non-toxic, protein-free, non-allergenic medicament for humans and warm-blooded animals.

The references herein to specific steps refer to the numbered steps of the claims herein.

BRIEF DESCRIPTION OF THE DRAWINGS

FIGS. 9–12 schematically illustrate mother and daughter forms for Q 17–X 24 representations.

FIGS. 16–18 schematically illustrate derived geometric figures as coordinates from crystal textures and forms of mother and daughter forms by addition, linkage and superposition.

FIG. 19 schematically illustrates the sequence of identifying the organs and organ zones associated with the crystal textures and forms.

DESCRIPTION OF THE PREFERRED EMBODIMENTS

Figure 1:
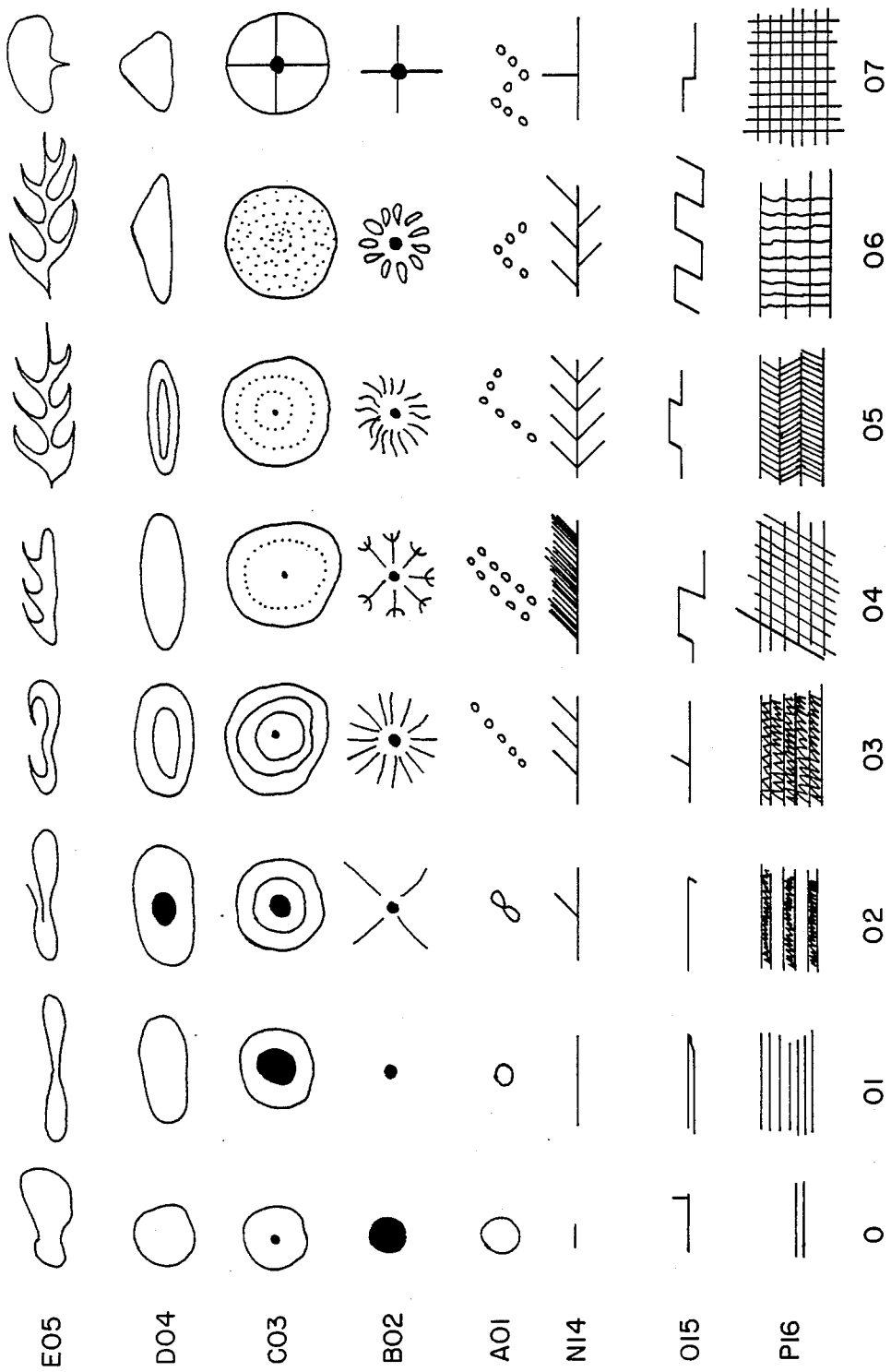
FIGS. 1–4 schematically illustrate mother and daughter forms for A 01–E 05 and N 14–P 16 representations.

A preferred embodiment of the method of the invention relates to the geometric and crystal morphological formation of the crystal textures and crystal forms of the method forms and daughter forms in the fixing of the biological coordinates in the descriptive definition of microscopically and photo-optically detected figures.

This embodiment also relates to geometric and crystal morphological figures as biological coordinates as crystal textures and crystal forms, which are derived from several mother- and/or daughter forms.

This preferred embodiment also relates to the crystallization of textures and forms in 3 defined regions from concentric circles, to which in these regions organs or organ zones are allocated in a particular, defined sequence from the outside inwards.

The method of the invention uses the following definitions:

Crystal textures are understood to be the areal aggregates, produced in the crystillization in step 8, of the crystal particles or needles.

Crystal forms are understood to be basic-, mother-, daughter- forms, which allow an unequivocal identification of the phenomenal figures.

Basic forms are understood to be simple, geometric figures, not able to be further reduced, as elements.

Mother forms are understood be be basic forms or their derivations, or homogeneously closed figures, or homogeneous, closed and identifiable crystal forms.

Daughter forms are understood to be forms derived from the mother forms as crystal textures.

In the crystallization according to step 8, free crystal structures can form, which do not form any systemic order amongst each other, such as in a lattice structure. The position direction of individual particles with respect to each other may be irregular. Such particles may cross each other or not touch each other.

Figures are understood to be typical, reproducible, defined crystal textures and crystal figures, which are visible microscopically and photo-optically, and which are characterized mathematically and descriptively and are thereby defined.

Reproducibility of the crystal textures and crystal forms is understood to be the visible, figurative conformity or similarity of form with multiple, chronologically independent repetition of the production of crystallizates from the homogeneous mixture of the distillate and of the soluble part of the calcinate from several drops from the same or comparable intitial substance.

It is to be noted here that blood is in constant equilibrium with the organs and organ tissues up to the removal of the quantity required to perform the method. This also applies to urine, taking into account the specialization of the elimination resulting through the function of the kidneys. The comparisons of the crystal textures from urine with those from clinically established findings produce consistent results in form, structure and information.

In these chronological intervals of removal, changes in the equilibrium continuously take place in the biological, dynamic process of the living individual. This means that the crystal textures and crystal forms which are made visible show changes in the overall picture. However, the reproducibility is maintained for the characteristic mother- and daughter forms. Through this, the rule is given for complete technical action, also for this removal of quantities of blood or urine which is to be analyzed.

Blood is understood to be the venous blood of humans or of warm-blooded animals.

The method of the invention is explained through the following example embodiment.

10 ml venous blood of a woman is mixed with 30 ml water which has been distilled three times, and the mixture is over-distilled at 96° C. with air cooling. The distillation is finished when the blood residue in the distillation flask is practically dry, i.e., the residue does not yield any more water under the same operating conditions. In the following method stage, the residue is heated in a porcelain crucible to 200° C. and is thereby dried. Thereafter, the residue is heated to 400° C., whereby intensively odorous gases form. Thereafter, the residue is heated to 600° C. and is consequently incinerated. The heating and incineration as calcination takes place in a closed muffle furnace, which is able to be regulated, without the supply of air as oxygen. The calcined residue is then cooled in the furnace to 150° C., is thereafter removed and pulverized in the mortar.

In the following method step, the distillate from step 1 is mixed with the calcined cake of blood from step 4. The mixture of both components is maintained under quiescent conditions at 20° C. ambient temperature for 8 hours for the formation of a homogeneous fluid mixture. Thereafter, the mixture is filtered through micro-fine filter paper.

In the following method step, the filtered solution is applied, at 20° C. regulated temperature, onto a glass microscope slide in 2 drops each of 0.08 ml, which form a diameter of 8 mm, and in approximately 20 min the water evaporates. Thereby, the formation of crystal textures and crystal forms takes place.

In the following method step, the reproducible and interpretable analysis of the blood picture is carried out in the microscopic dark field with gradual enlargement of 12.5, 25, 160, and 400 times. These microscopic images are photographed for documentation.

In the following method step, the analogy comparison takes place of the defined textures and forms of the blood picture with those of an established pathogenic condition to determine the disease condition.

This analogy comparison may also take place for example with standard types from comparative series, in order to determine the physiological, metabolic and pathlogical condition.

In a further method step, an auto-vaccine is produced from 7 ml of the filtered solution with the addition of 23 ml of isotonic, physiological solution and 20 ml of 40% ethyl alcohol. This medicament has the commercial name HOMODOT.

With about 7 ml filtered solution the mixture ratio of filtered solution:isotonic, physiological solution:ethyl alcohol (40 vol.-%)=1:5:4.

In another embodiment of these further method steps a drop of venous blood is removed from this woman and is injected on a blood agar base and after incubation at a temperature of 37° C. for 38 hours an anti-vaccine of 2 ml is withdrawn.

This matter is then mixed with 20 ml water which has been distilled three times, and the mixture is then distilled. The residue is then calcined in accordance with method steps 2 at temperatures up to 200° C., 400° C., 600° C. and is then pulverized and mixed with the distillate. After a period of maintenance under quiescent conditions for 2 hours, the mixture is filtered. The filtrate of 6 ml is mixed with 14 ml of physiological solution and 20 ml of 40% ethyl alcohol. This microbiologically cultured auto-vaccine is a non-toxic, protein-free and non-allergenic medicament.

This medicament has the commercial name ANTIHOMODOT. This is used for the specific simulation of chronic, toxic and parasitogenic foci in the body of this woman.

The dilution of the blood with water in step 1 takes place in order to produce sufficient steam pressure for the distillation and in order to have sufficient solution in which the calcinate from steps 2 to 4 is dissolved in steps 5 to 6 to a homogeneous phase. The ratio of blood to water of 1:2.5 to 3.5 represents a preferred range. If less than 2.5 times is used, then particularly in the case of highly viscous blood too little steam pressure is produced and hence too little distillate. In so far as over 3.5 times is used with low viscous blood, too high a fluid component occurs in the crystillizate in step 8 and hence an insufficient formation of the crystal textures.

The final temperature of 600° C. to be used in step 2 represents a further selection. Adhering to the temperature rise according to step 2 produces an optimum definition of the crystallizate in step 8. With too low a temperature, the crystallizate becomes coarse, and with too high a temperature it becomes too fine grained and consequently leads to an insufficient formation of the forms.

The analysis of the crystal textures place in step 9 in the microscopic dark field. With 10–15 times enlargement, an overall picture is produced for delimination of the regions (A), (B), (C) of FIG. 19.

With 20–50 times enlargement, an image section and an image point are brought into coincidence as vertex on the left abscissa and are taken up optically as region (A) for analytical evaluation.

In the same way, the regions (B) and (C) are determined and evaluated analytically.

With 60–160 times enlargement, within the regions the compact, areal and/or spatial dendrites are determined analytically as crystal textures and crystal forms. These are then evaluated diagnostically in relation to organ, after their optical isolation.

With 180–800 times enlargement, the representation and identification of the morphological, geometric, spatial basic forms takes place.

These basic forms are related as defined figures to biologically relevant cations, in particular to Na, K, Mg, Ca. These basic forms show dominant metabolic processes as an expression of an oversaturation of the tissue. Pathogenic metabolic conditions are diagnosed therefrom.

In step 10, the microscopic and photooptical evaluation as analogy comparison of the crystal textures and crystal forms defined in step 9 produces an established diagnosis of the condition of health or disease of human or animal. Such pathological conditions are, for example, chronic, rheumatic leukemia.

The figurative representation of the crystal textures and crystal forms is produced according to the method of the invention from this established pathological condition. Through the coincidence of the mother-, daughter- and basic forms from the crystal textures and forms of the figurative representation of the diseased person with those from the figurative representation from the established pathological condition, the pathological disease condition of the person under examination is unequivocally diagnosed through this coordination.

For example, 10 different crystallizates of leukemia of persons under examination produce the same, common, characteristic features in the mother-, daughter-, basic forms in addition to differing figures from the differing conditions of the diseases of these persons.

In a preferred embodiment, the calcination in step (2) takes place in three stages at temperatures of 200° C., 400° C., 600° C. such that first heating takes place linearly to 200° C. and operations are kept constant at this temperature for 5 to 10 minutes. This mode of operation is repeated at 400° C. and at 600° C. Cooling is then accomplished as set forth in step (3).

This embodiment allows calcination to take place in stages linearly in order to control the smoke development in the stages.

The method of the invention is described through figures of the mother and daughter forms of the crystal textures and crystal forms in tabulated form with biological coordinates. The mother forms are represented on the ordinates at the abscissa "0". The daughter forms are represented on the abscissae 01–27 to the ordinates A 01–$Z_4$ 30.

This figurative representation corresponds to the microscopic and photo-optical evaluation of the crystal textures and crystal forms of clinically established disease conditions in multiple repetition.

| FIG. forms: | Representation: Abscissa | Mother and daughter |
|---|---|---|
| | | Ordinates |
| 1 | A 01–E 05<br>N 14–P 16 | 0–07 |
| 2 | " | 08–15 |
| 3 | " | 16–23 |
| 4 | " | 24–27 |
| 5 | F 06–M 13 | 0–07 |
| 6 | " | 08–15 |
| 7 | " | 16–23 |
| 8 | " | 24–27 |
| 9 | Q 17–X 24 | 0–07 |
| 10 | " | 08–15 |
| 11 | " | 16–23 |
| 12 | " | 25–27 |
| | | Mixed forms: |
| 13 | Y 25–$Z_4$ 30 | 0–07 |
| 14 | " | 08–15 |
| 15 | " | 16–23 |

The method of the invention will be further explained by way of example. Example for photographs with the enlargements according to step 9.

| FIG. | Representation |
| --- | --- |
| 20 | Enlargement 12.5 times: Overall image of the crystal textures, |
| 21 | Enlargement 25 times : illustration of the sectors, |
| 22 | Enlargement 65 times : areal illustration of the dendrite form, |
| 23 | Enlargement 160 times : areal illustration of the geometric basic form. |

Examples for the analogy comparison of the blood of a man according to step 10 with the coordinates of an established, pathological condition for diagnosis of the disease condition.

Through optical comparison of the crystal structures and crystal forms, the following coordinates are determined for the blood of the sick person:

| FIG. | Coordinates |
| --- | --- |
| 24 | Region (A) : D 04-0 (C 03-13) + B 03-0 + D 04-014, Region (B) : D 04-04 + D 04-11 + K 11-12 Region (C) : $Z_1$27-01 (K 11-12 + K11-13 (K 11-12 + K 11-13 + K 11-09) |
| 25 | Region (A) : E 05-11 + E 05-22 + N 14-03, Region (B) : B 02-04 + M 13-20, Region (C) : N 14-20 + B 02-5, |
| 26 | Region (A) : (M 13-16, N 14-24 + K 11-09 ) x Z 1, 27-0, Region (B) : M 13-20+ 15-20 + 0 15-18, Region (C) : E 05-11 + M 13-25, Region (A) : Z 1,27-02 (N 14-11 + N14-20 + G 7-14) Region (B) : M 13-0 (M 13-20 + N 14-20) Region (C) : N 14-21 (N 14-20). |

These coordinates correspond to the textures and forms of the crystallizates determined experimentally from established pathological disease.

Examples of the crystal textures and crystal forms of an assured, pathological disease condition as photographs for the analogy comparison with the crystallizate from step 8 of blood of a disease to be diagnosed according to step (10).

| FIG. | Disease condition |
| --- | --- |
| 28 | Textures and forms of the blood of a 39 year old man : chronic-rheumatic leukemia : coordinates : C 03-0, C 03-12, C 03-18, |
| 29 | Blood of a woman whose disease is to be diagnosed. Coordinates : C 03-0, C 03-12, C 03-18. Disease diagnosed according to step 10 : acute, chronic-rheumatic leukemia. |

-continued

| FIG. | Disease condition |
| --- | --- |
| 30 | Blood of a woman whose disease is to be diagnosed. Coordinates : C 03-0, C 03-12, C 03-18. Disease : chronic-rheumatic leukemia. |

Figure 28:
FIG. 28 is a photograph which contains the crystal structures and forms of the blood of a patient with leukemia.

Explanations:

FIG. 28: Condition in Stage 5 of the disease (moribund). The disk-like layers show the gradual character of the disease in the entire body.

Figure 29:
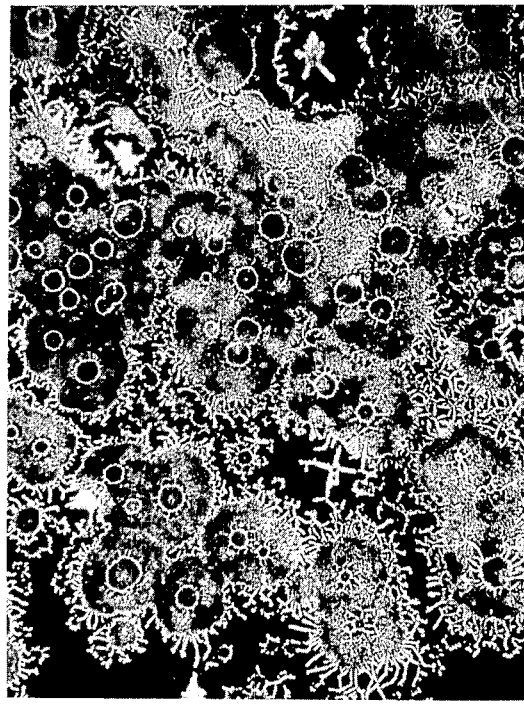
FIGS. 29 and 30 are photographs which contain the crystal structures and forms of the blood of patients to be diagnosed.

FIG. 29: Condition in Stage 4 with mestastasization of the acute, chronic-rheumatic leukemia. Proven through the enlargement of the crystal form C 03-18.

Figure 30:
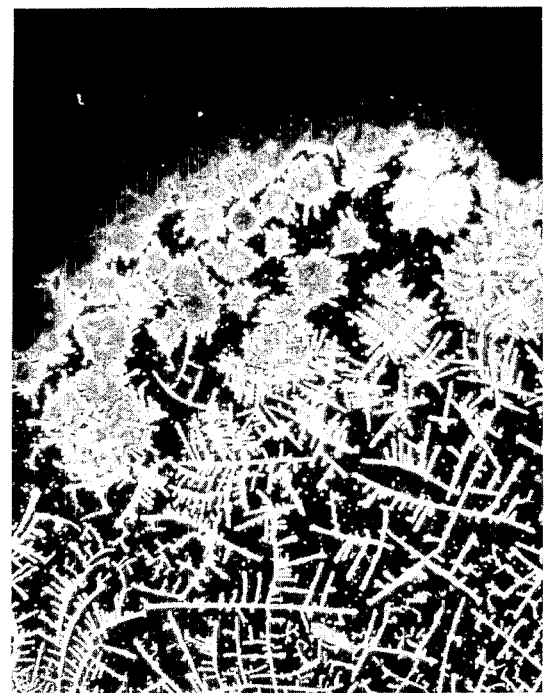
Figure 31:
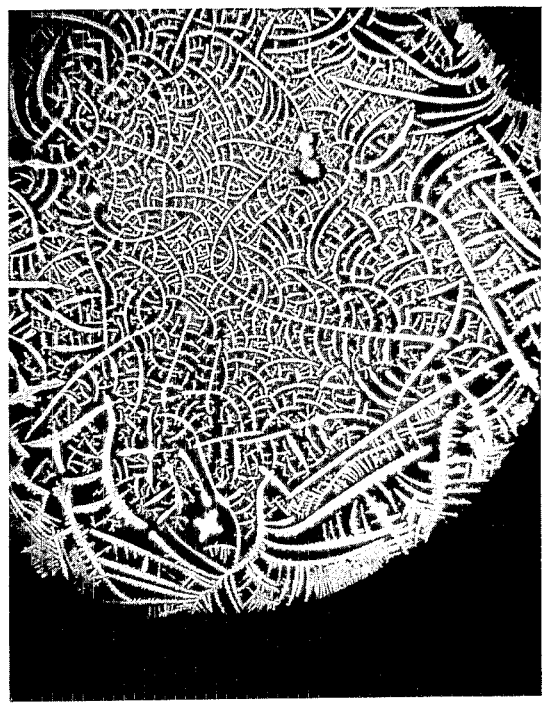
FIGS. 31 and 32 are photographs which contain the crystal textures and forms of the blood of a patient with enteritis, articular rheumatism and pancreatitis.
Figure 32:
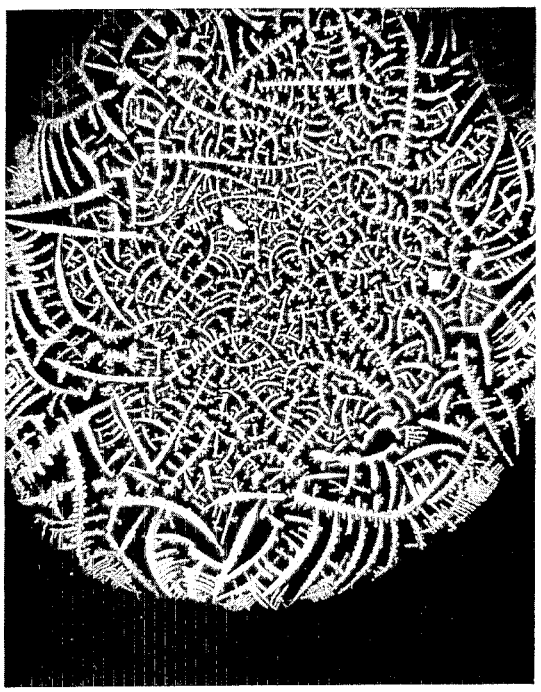
Figure 33:
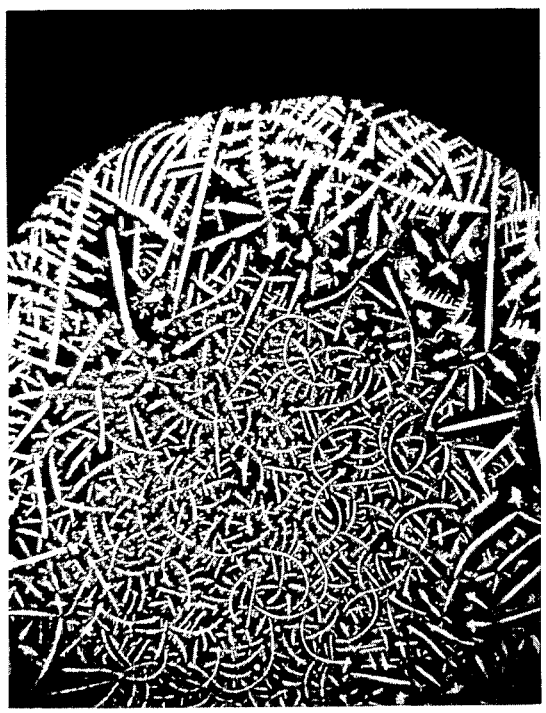
FIGS. 33–36 are photographs which contain the crystal textures and forms of the blood of a man with a weakness of liver function with the beginning of nephrosclerosis.
Figure 34:
Figure 35:
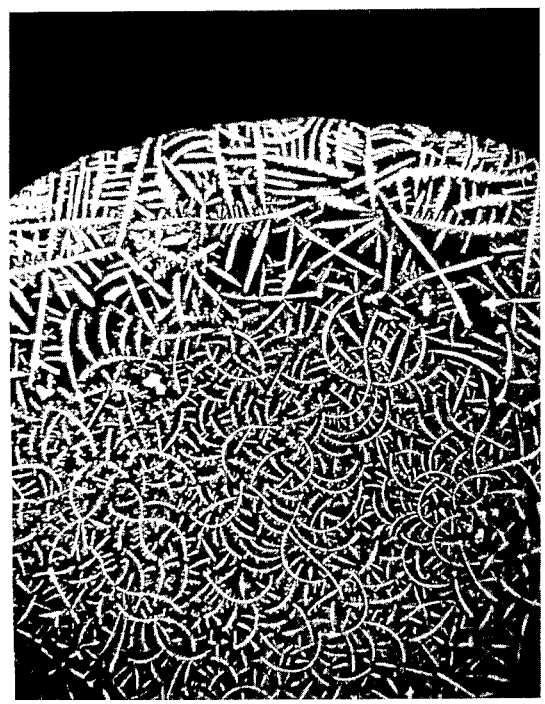
Figure 36:
Figure 37:
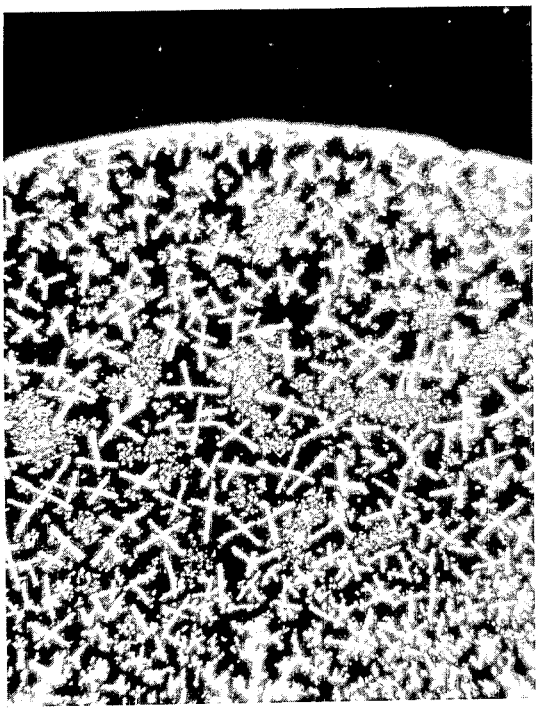
FIG. 37 is a photograph which contains the characteristic crystal textures for osteomyelofibrosis.
Figure 38:
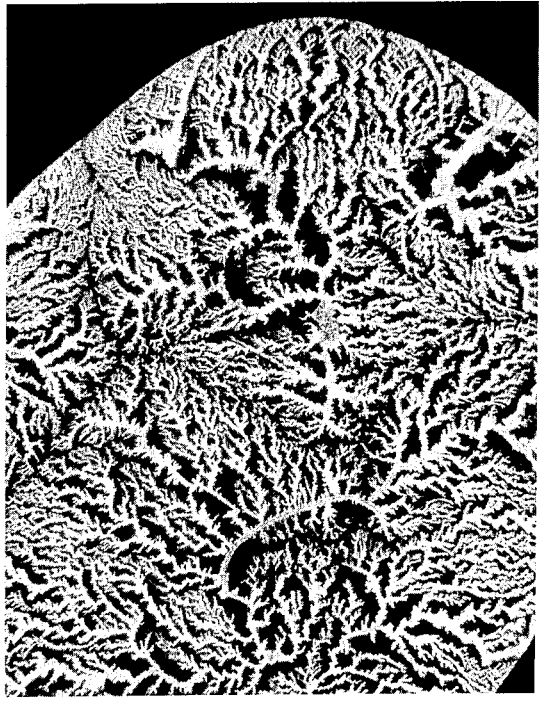
FIG. 38 is a photograph which contains the characteristic crystal textures for nephrosis in AIDS.
Figure 39:
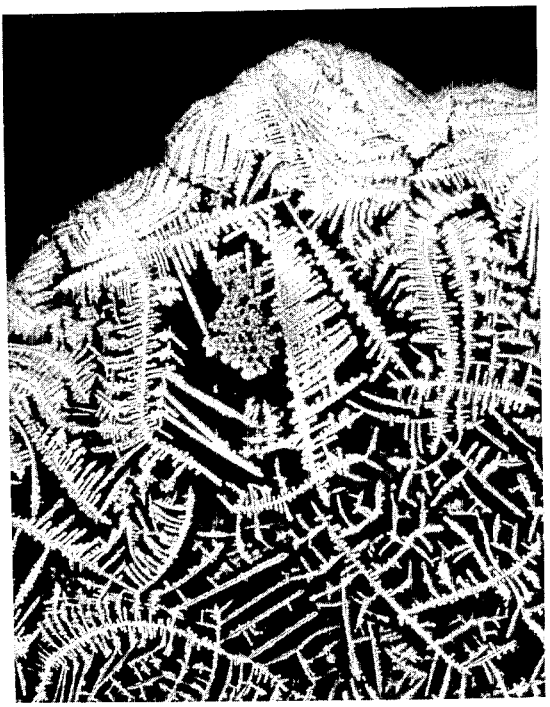
FIG. 39 is a photograph which contains the characteristic crystal textures for mamma carcinoma Stage 4.
Figure 40:
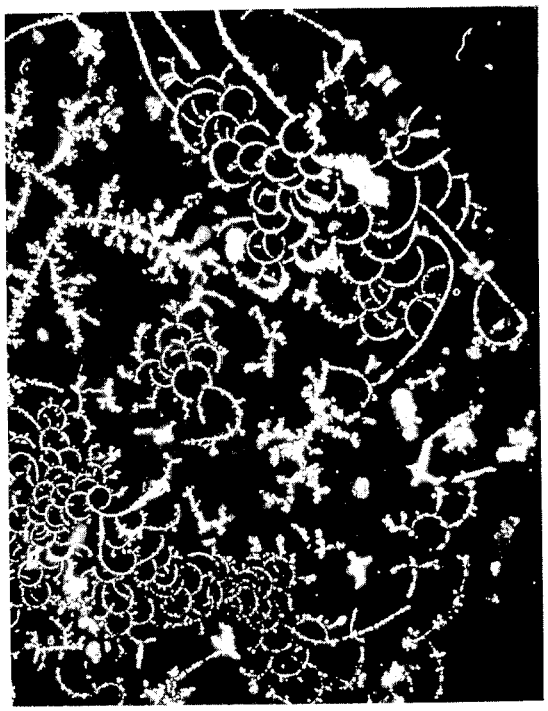
FIG. 40 is a photograph which contains the characteristic crystal textures for cirrhosis of the liver.
Figure 41:
FIG. 41 is a photograph which contains the characteristic crystal textures for open tuberculosis.
Figure 42:
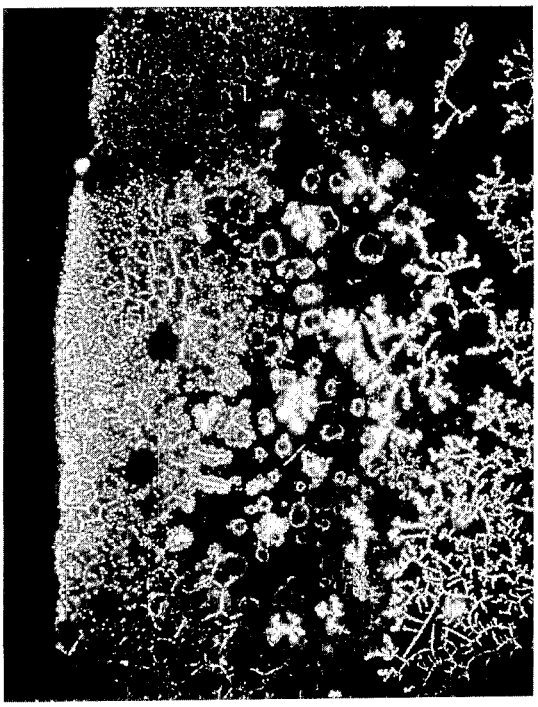
FIG. 42 is a photograph which contains the characteristic crystal textures for syphilis.
Figure 43:
FIG. 43 is a photograph which contains the characteristic crystal textures for myelotic leukemia.
Figure 44:
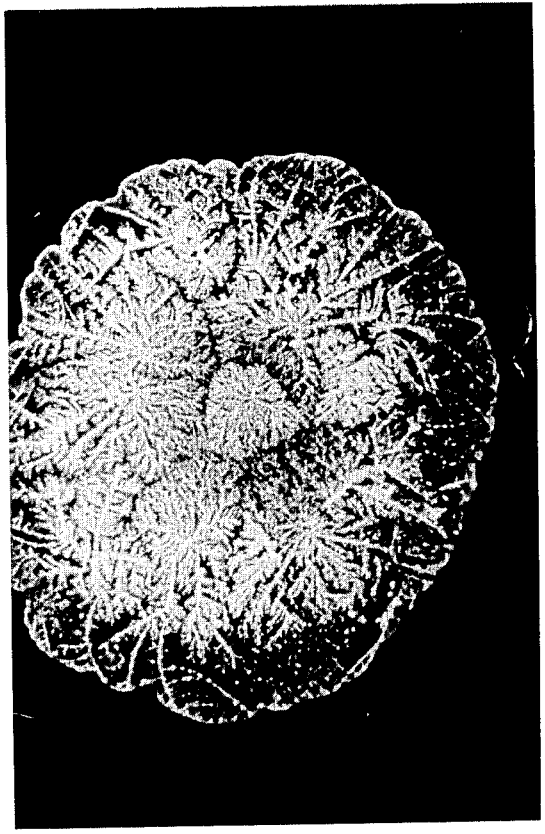
FIG. 44 is a photograph which contains the characteristic crystal textures for cerebellum atrophy.

FIG. 30: Condition in Stage 3 with simultaneous mycotisation of region (A) represented on the corona of form C 03-18 and C 03-0.

The further forms on these photographs do not relate to the diagnosed clinical picture, but rather to the individual physiology or respectively the specific and individual, secondary consequences of the disease.

The following photographs relate to the reproducibility of the crystal textures and crystal forms of a blood picture after division into 2 fractions.

These photographs relate to the blood of a man with enteritis, and articular rheumatism and pancreatitis.

| FIG. | Coordinates of the crystal textures: |
| --- | --- |
| 31 + 32 | Region (A) : Q 17-15, E 05-15. , M 13-13, Region (B) : E 05-10, Q 17-16, T 20-22, Region (C) : Not applicable. |

The following photographs relate to the reproducibility of the crystal textures and crystal forms after the division of the blood into 4 fractions. These illustrations relate to the blood of a man with a weakness of liver function with the beginning of nephrosclerosis.

| FIG. | Coordinates of the crystal textures: |
| --- | --- |
| 33 + 34 + 35 + 36 | Region (A) : Dominant form : Q 17-05, 0 15-20, Region (B) and Region (C) : Dominant form : L 12-0, M 13-0. Both forms with the branch type : N 14-16. |

The incorporations in Region (B) demonstrate a kidney concrement.

The reproducibility with the same disease with different persons is confirmed for example by the

| FIG. | |
| --- | --- |
| 28 + | clinically established condition, |
| 29 | diagnosed condition which is established through the optical analogy comparison of the crystal textures and crystal forms, |
| 30 | The same as Illustration 10. |

The photographs set out below demonstrate by way of example the characteristic crystal textures for clinically established diseases.

These photographs are used in the analogy comparison according to step 10.

| FIG. | Disease |
|---|---|
| 37 | Biological coordinates Osteomyelofibrosis, characteristic texture : (N 14–10 + C 03–25), |
| 38 | Nephrosis in Aids : characteristic texture : M 13–20 (E 05–15), |
| 39 | Mamma carcinoma Stage 4, characteristic texture : honeycomb formation, type : K 11—11, |
| 40 | Cirrhosis of the liver, characteristic texture : L 12–(01–04), |
| 41 | Open tuberculosis characteristic texture : C 03–02, C 03–11, B 02–03, |
| 42 | Syphilis, characteristic texture : Y 25–09 (K 11–01 + C 03–15), |
| 43 | Myelotic leukemia, characteristic texture : (M 13–03 + Q 17–05), V 22–03. |
| 44 | Cerebellum atrophy, characteristic texture : (S 19–12) Y 25–10. |

Figure 45:
FIG. 45 is a photograph which contains the characteristic crystal textures for chronic bronchitis.
Figure 46:
FIG. 46 is a photograph which contains the characteristic crystal textures for actue nephritis.
Figure 47:
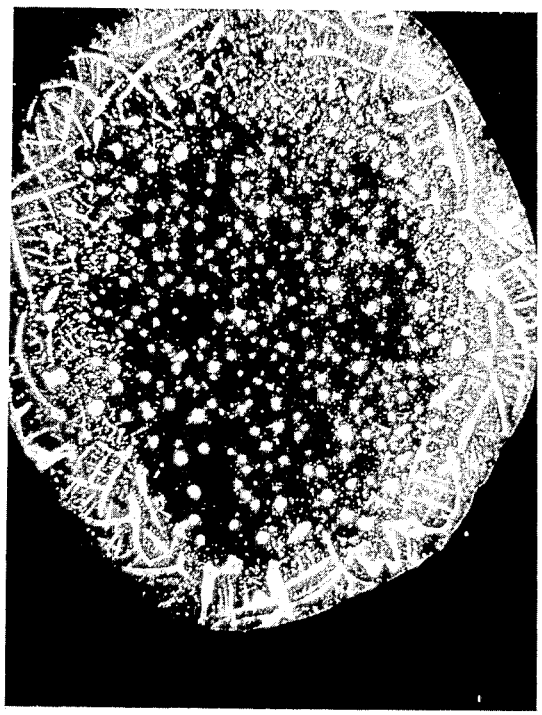
FIG. 47 is a photograph which contains the characteristic crystal textures for motor paralysis.
Figure 48:
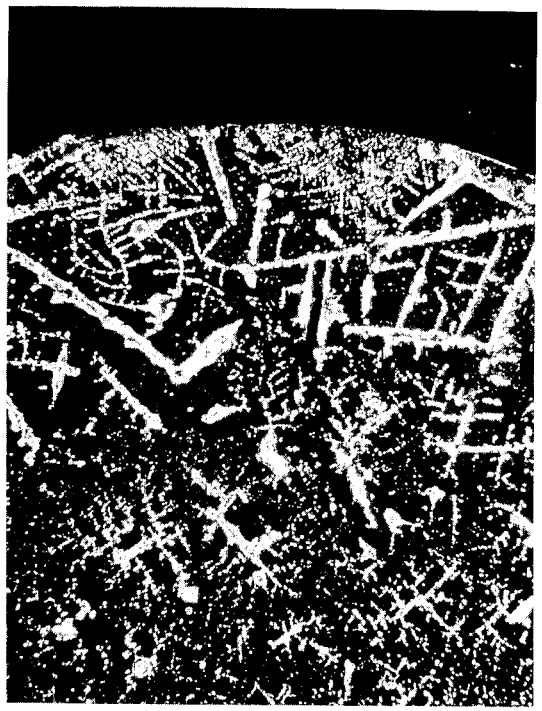
FIG. 48 is a photograph which contains the crystal textures for kidney infection.
Figure 49:
FIG. 49 is a photograph which contains the crystal textures for neophrosis and hepatosis.

The FIGS. 45 and 46 are produced from human urine of an infant as starting material according to the method of the invention.

| FIG. | Disease |
|---|---|
| 45 | Biological coordinates Chronic bronchitis Characteristic texture : Region A : $Z_1$ 27–05, Region B : n(N 14–10) (N14–11) |
| 46 | Acute nephritis Characteristic texture : Region B : n(N 14–12) (0 15–20) |

The following example which illustrates the method of the invention uses urine as starting material. Urine analyses are used when the taking of a sample of blood is difficult, as in the case of infants or persons with a risk of thrombosis or in the presence of scarred veins.

Venous blood contains the metabolic products in dissolved form. This also applies to urine as elimination product and carrier of metabolic products.

10 ml urine from the mid-stream of a child are mixed with 30 ml water which has been distilled three times, and the mixture is distilled at 96° C. with air cooling. The distillation is finished when the residue is practically dry.

In the following method stage, one proceeds in the same way as with blood, and calcination takes place. The calcinate is cooled in the furnace to 150° C., is then removed and ground in the mortar to a fine-grained or soft matter. In the following method step, the distillate from step 1 is mixed with the calcinate from step 4. The mixture is maintained under quiescent conditions for 16 hours at 20° C. until a homogeneous phase is formed. This is then filtered through microfine filter paper. In the following method step, one proceeds as with blood for the formation of the crystal textures and crystal forms. In the following method step, as with blood, analysis takes place in the microscopic dark field with the same gradual enlargement, and the representation is fixed photo-optically.

Therefore, the same results are obtained in steps 9 and 10 with urine as with blood.

In a further method step, as with blood, a medicament is produced as an autovaccine, with the same mixture ratios, and which is given the commercial name HOMODOT.

In an alternative embodiment of this method step, a drop is removed from the child's urine, this is injected on a blood agar base and incubated at a temperature of 37° C. An anti-vaccine of 2 ml is withdrawn after 48 hours. One then proceeds with this substance as with blood. The resulting medicament is given the commercial name ANTIHOMODOT. This is used for the specific simulation of chronic, toxic and parasitogenic foci in the body of this child.

The formation of the crystal textures or crystal forms takes place with animal blood or urine in an analogous manner.

The following photographs are produced from animal blood of horses as starting material according to the method of the invention.

| FIG. | Disease |
|---|---|
| 47 | Biological coordinates Motor paralysis Characteristic texture : Region A : M13–11, M13–16; Region B and C : K11–12. |
| 48 | Kidney infection Characteristic texture : Region A : N14–24, $Z_1$27–01. Region B : F06–23, $Z_1$27–11 |
| 49 | Nephrosis and hepatosis Characteristic texture : Region A : M13–20, D04–07; Region B : (E05–12) (M13–20) Region C : (N14–15) (M13–20). |

FIG. 19 demonstrates the sequence of organs and organ zones from the outside inwards defined in the concentric regions, and namely in the endodermal region (A), in the mesodermal region (B) and in the ectodermal region (C).

This establishing of localization takes place through optical evaluation of the crystal textures and crystal forms, which are produced according to the method of the invention. These textures and forms are produced from the blood of clinically established clinical pictures of persons.

Through the allocation, it is surprisingly possible to determine and define the sequence and the location, from which these diseases are to be recognized from the figures of the textures which are characteristic of them.

The reproducibility of the allocation results in that the blood of several persons with the same established disease, is analyzed.

Figure 4:
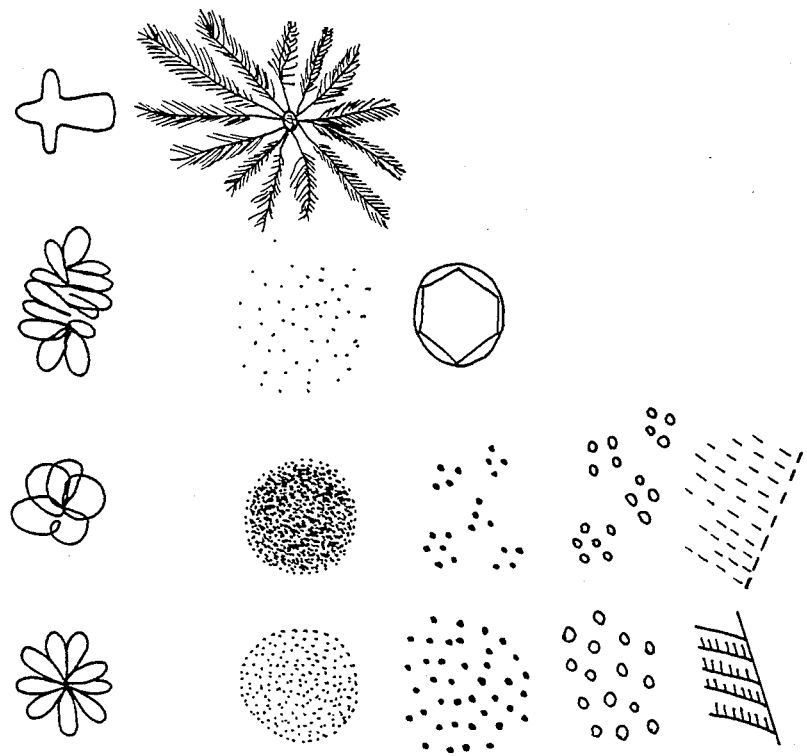

These function circles (A), (B), (C) are also shown in FIG. 4. These figures show, in reciprocal representation with respect to nature, these regions in the concentric zones. They show in these regions the topology of the organs and organ zones.

The preferred coordinates are also represented in the following figures:

| FIG.: | Coordinates: |
|---|---|
| 13 | $Y_25-(01-07)$ |
|  | $Z_026-(01-07)$ |
|  | $Z_127-(01-07)$ |
|  | $Z_228-(01-07)$ |
|  | $Z_329-(01-07)$ |
|  | $Z_430-(01-07)$ |
| 14 | $Y_25-(08-15)$ |
|  | $Z_026-(08-15)$ |
|  | $Z_127-(08-15)$ |
|  | $Z_228-(08-15)$ |
|  | $Z_329-(08-03)$ |
|  | $Z_430-(08-15)$ |
| 15 | $Y_25-(16-23)$ |
|  | $Z_127-(16-23)$ |
|  | $Z_228-(16-20)$ |
|  | $Z_329-(16-17)$ |

The further preferred coordinates are represented in the following figures:

| FIG.: | Coordinates: |
|---|---|
| 16 | $Z_127-15$: |
|  | (C03–09) + (N14–18) + (V22–06) |
| 17 | $Z_127-16$: |
|  | n(D04–00) + (Q17–06 + A01–24) |
| 18 | $Z_127-09$: |
|  | (K11–03) (T20–00/W23–00/ |
|  | W23–17/C03–23/C03–00) |

FIGS. 16 to 18 derived geometric figures as coordinates from crystal textures and crystal forms of mother forms and daughter forms by addition, linkage and superposition.

FIG. 19 represents within the three concentric circles the sequence of reading from the outside inwards the organs and organ zones associated with the crystal textures and crystal forms.

The carrying out of the method of the invention for early diagnosis and for the production of the medicament is ecologically positive, because no toxically effective substances, such as chemicals, are required and consequently no residues arise therefrom.

Through the possibility of early detection of disease conditions in humans and animals, the method of the invention is of considerable significance for medical science and practice. Through the prompt therapy of diseases, this enables costs to be lowered compared with those in the case of advanced disease conditions. The method of the invention is therefore also to be attributed a considerable economic significance.

According to the state of the medical treatment of diseases, a plurality of partially costly diagnostic methods are necessary to establish them. However, the method of the invention allows early diagnosis to be carried out rapidly and safely by a mode of operation which is able to be carried out technically in a simple manner with equipment with low investment costs and if required allows the detected diseases to be treated therapeutically with medicaments produced from the same blood.

The method of the invention therefore permits several parameters to be taken up reproducibly with an apparatus for a qualitative representation as a whole.

I claim:

1. Method for the crystal morphological analysis of blood or urine of a human, vertebrate or mammal for early diagnosis comprising:
   (1) distilling a mixture of (a) human blood, human urine, or the blood or urine of a warm blooded animal with (b) distilled water, said mixture being in a volume ratio of blood or urine to water of 1:2.5 to 3.5 to provide a distillate and a dry cake of blood or urine sediment;
   (2) calcining the dry cake by heating at a constant rate for a period of 60 to 70 minutes to a temperature of about 600° C. to provide a calcinate;
   (3) cooling the calcinate for a period of about 2 to 4 hours to a temperature of about 150° C.;
   (4) pulverizing the cooled calcinate;
   (5) mixing the distillate from step (1) with the pulverized calcinate;
   (6) maintaining the mixture of step (5) under quiescent conditions for a period of 8 to 16 hours to provide a homogeneous fluid mixture;
   (7) filtering the homogeneous fluid mixture;
   (8) forming crystals from the filtered mixture on glass microscope slides by applying drops with a diameter of 6 to 10 mm of the filtered mixture onto the glass slides under conditions of relative humidity of about 40 to 60% and a temperature of about 20° C. and evaporating the water from the drops at a temperature of about 20° C. to provide on the glass slide crystals with an outer concentric annulus designated the endodermal region (A) of FIG. 19, a middle concentric annulus designated the mesodermal region (B) of FIG. 19 and a central annulus designated the ectodermal region (C) of FIG. 19;
   (9) microscopically analyzing the form and texture of the crystals in the microscopic dark field with
      (a) an enlargement of 10 to 15 times to show the regions over-all;
      (b) an enlargement of 20 to 50 times to show the individual form and texture of regions (A), (B) and (C),
      (c) an enlargement of 60 to 160 times to show the form and texture of the compact, areal and/or spatial dendrites; and
      (d) an enlargement of 170 to 800 times to show the dendrite images with morphological, geometric, spatial basic forms for the identification of the crystal-forming basic forms; and
   (10) comparing the microscopic analysis of step (9) with a series of established pathological microscopic standards or with the coordinates of mother- and daughter forms to provide a diagnosis of the condition of health or disease of the human, vertebrate or mammal.

2. Method according to claim 1, wherein a quantity of 3 to 15 ml of human or animal blood or urine is used in step (1).

3. Method according to claims 1 or 2, wherein the calcination in step (2) takes place in 3 stages at temperatures of 200°, 400°, 600° C. such that first heating takes place linearly to 200° C. and operations are kept constant at this temperature for 5 to 10 min., and this mode of operation is repeated at 400° C. and then at 600° C., and thereafter cooling takes place in accordance with step (3).

Figure 5:
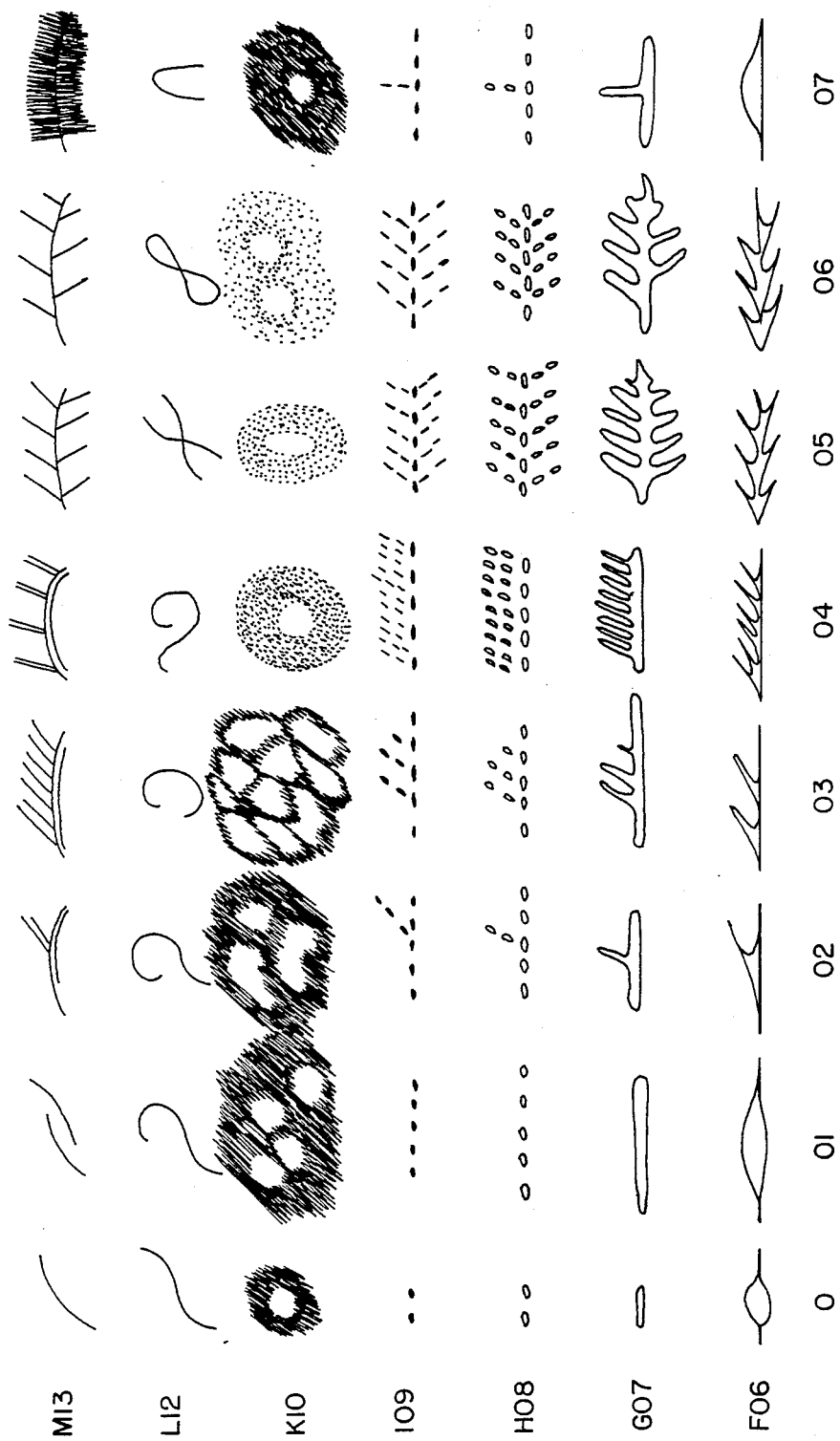
FIGS. 5–8 schematically illustrate mother and daughter forms for F 06–M 13 representations.
Figure 6:
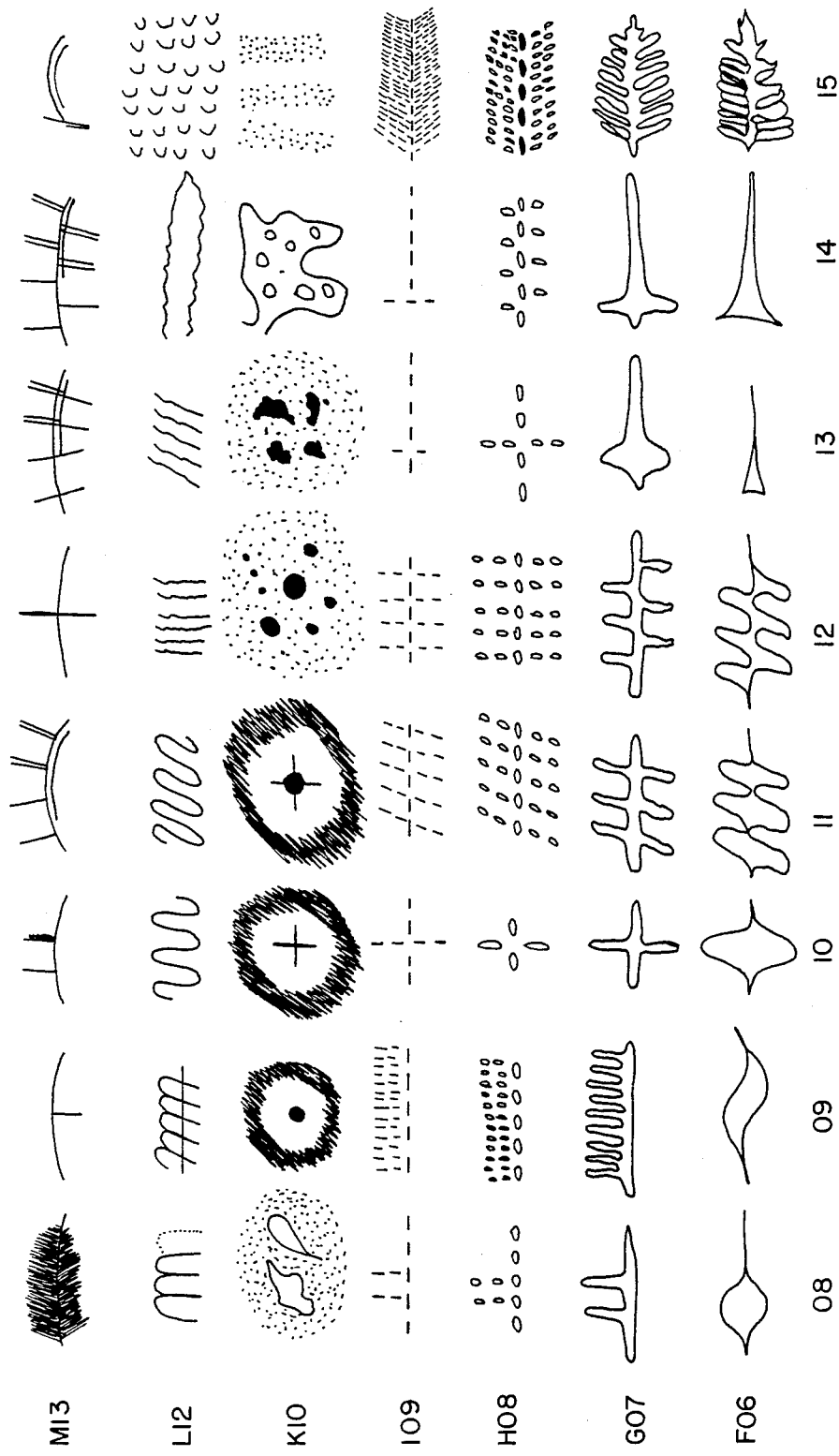
Figure 7:
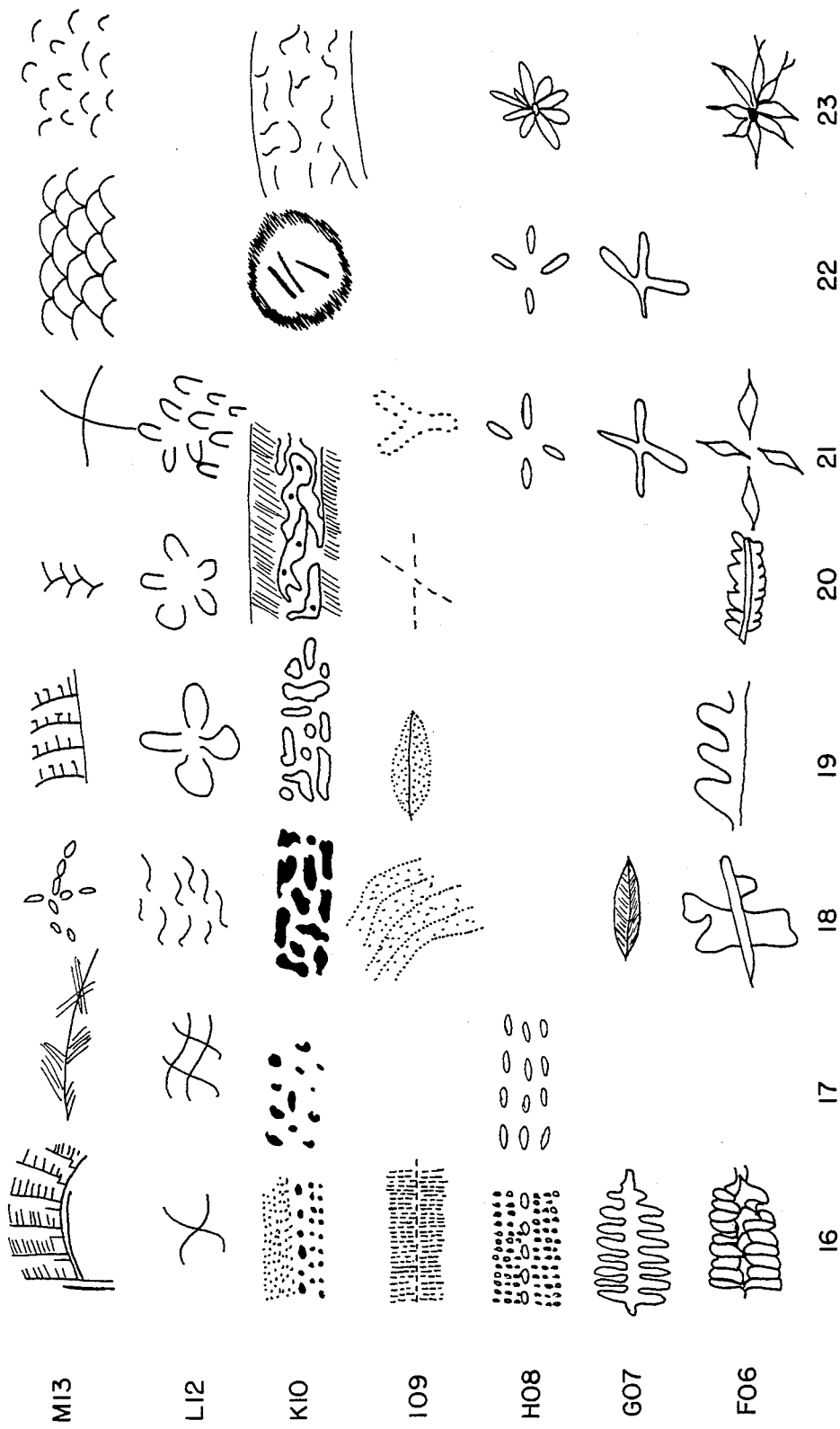
Figure 8:
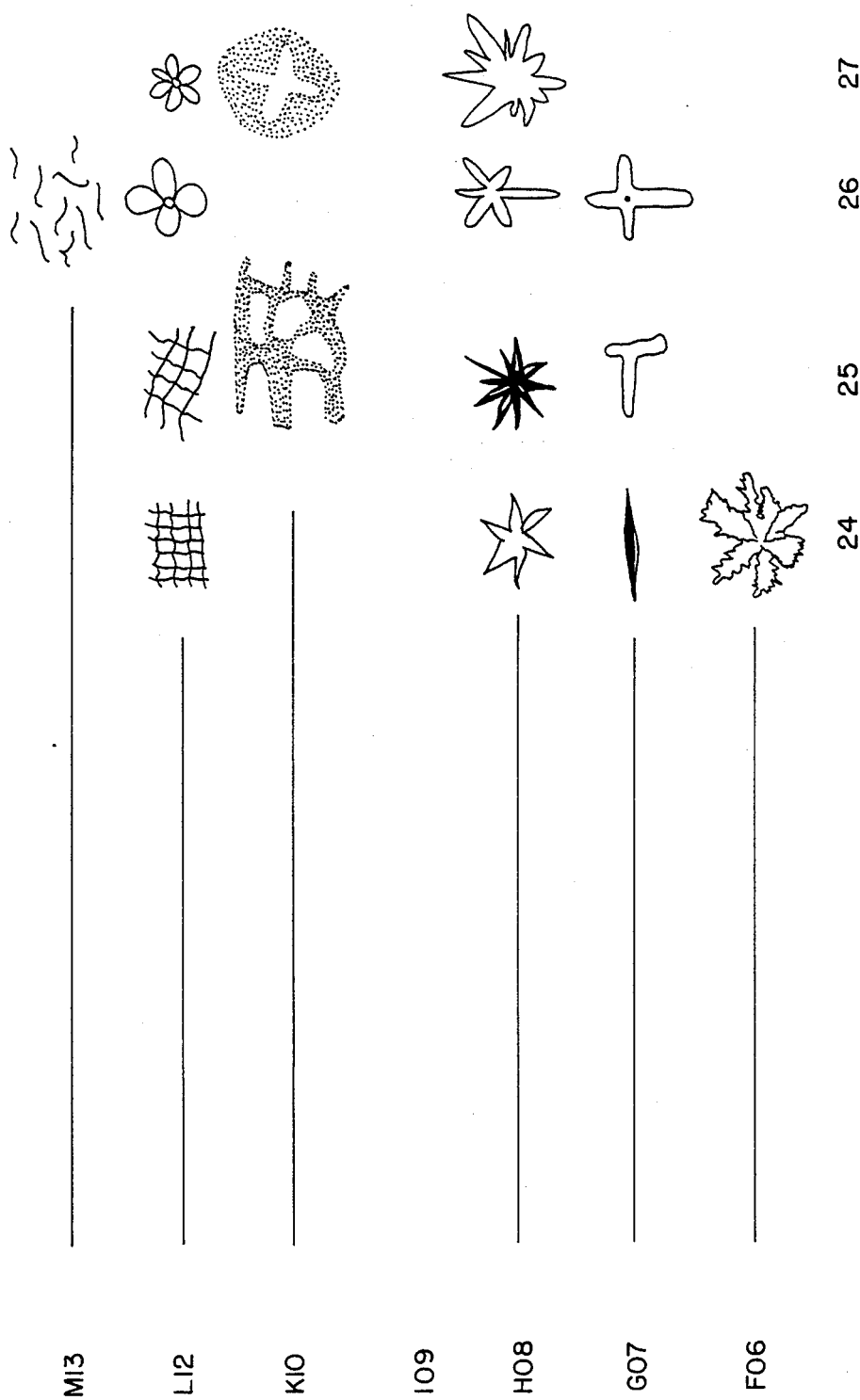
Figure 9:
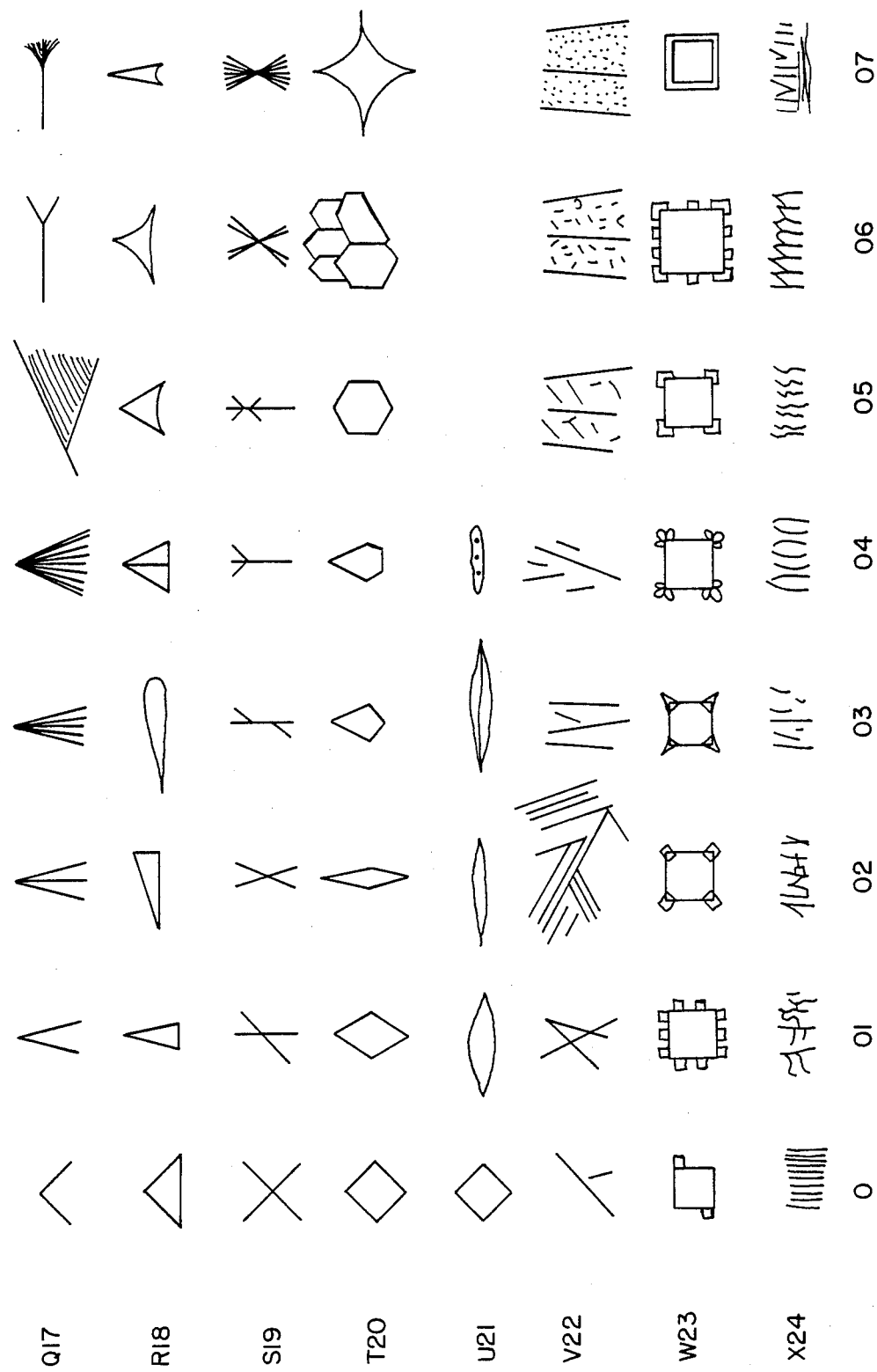

4. Method according to claim 1, wherein the crystal textures and crystal forms have the following mother forms as geometric, morphological figures:

| | |
|---|---|
| 0 - A 01 = | empty circle with maximum diameter of 0.2 mm on the slide, as shown in FIG. 1, |
| 0 - B 02 = | filled circle of 0 to a maximum 2 mm diameter on the slide, as shown in FIG. 1, |
| 0 - C 03 = | empty circle with small, filled circle area in the interior with any diameter, as shown in FIG. 1, |
| 0 - D 04 = | empty circle, diameter greater than 0.2 mm on the slide, as shown in FIG. 1, |
| 0 - E 05 = | drop-like shape with rounding on both longitudinal sides, as shown in FIG. 1, |
| 0 - F 06 = | oval extended shape with point-shaped longitudinal ends, as shown in FIG. 5, |
| 0 - G 07 = | compressed, empty circle with parallel longitudinal sides and round ends, as shown in FIG. 5, |
| 0 - H 08 = | 2 compressed, empty circles, as shown in FIG. 5, |
| 0 - I 09 = | 2 small, slightly compressed, filled circles, as shown in FIG. 5, |
| 0 - K 10 = | inner circle in a diffuse or geometrically ordered area, as shown in FIG. 5, |
| 0 - L 12 = | sinusoidal line, as shown in FIG. 5, |
| 0 - M 13 = | circular limiting line of a segment, as shown in FIG. 5, |
| 0 - N 14 = | simple line form, as shown in FIG. 1, |
| 0 - O 15 = | lines with squared-off pieces, as shown in FIG. 1, |
| 0 - Q 17 = | angle form, as shown in FIG. 9, |
| 0 - R 18 = | triangle form, as shown in FIG. 9, |
| 0 - S 19 = | crossing form, as shown in FIG. 9, |
| 0 - T 20 = | quadrilateral form, as shown in FIG. 9, |
| 0 - U 21 = | broken quadrilateral form, as shown in FIG. 9, |
| 0 - V 22 = | larger lines with connected and unconnected, smaller angled line, as shown in FIG. 9, |
| 0 - W 23 = | larger rectangular forms with smaller, angular addition on the outer sides, as shown in FIG. 9, |
| 0 - X 24 = | transverse band form, as shown in FIG. 9. |

5. Method according to claim 4, wherein the crystal textures and crystal forms of the daughter forms derived from the mother forms have the following geometric and morphological figures:

mother forms (1): $x=0$; $y=n$
daughter forms (2): $x=(01-m)$; $y=n$

Figure 2:
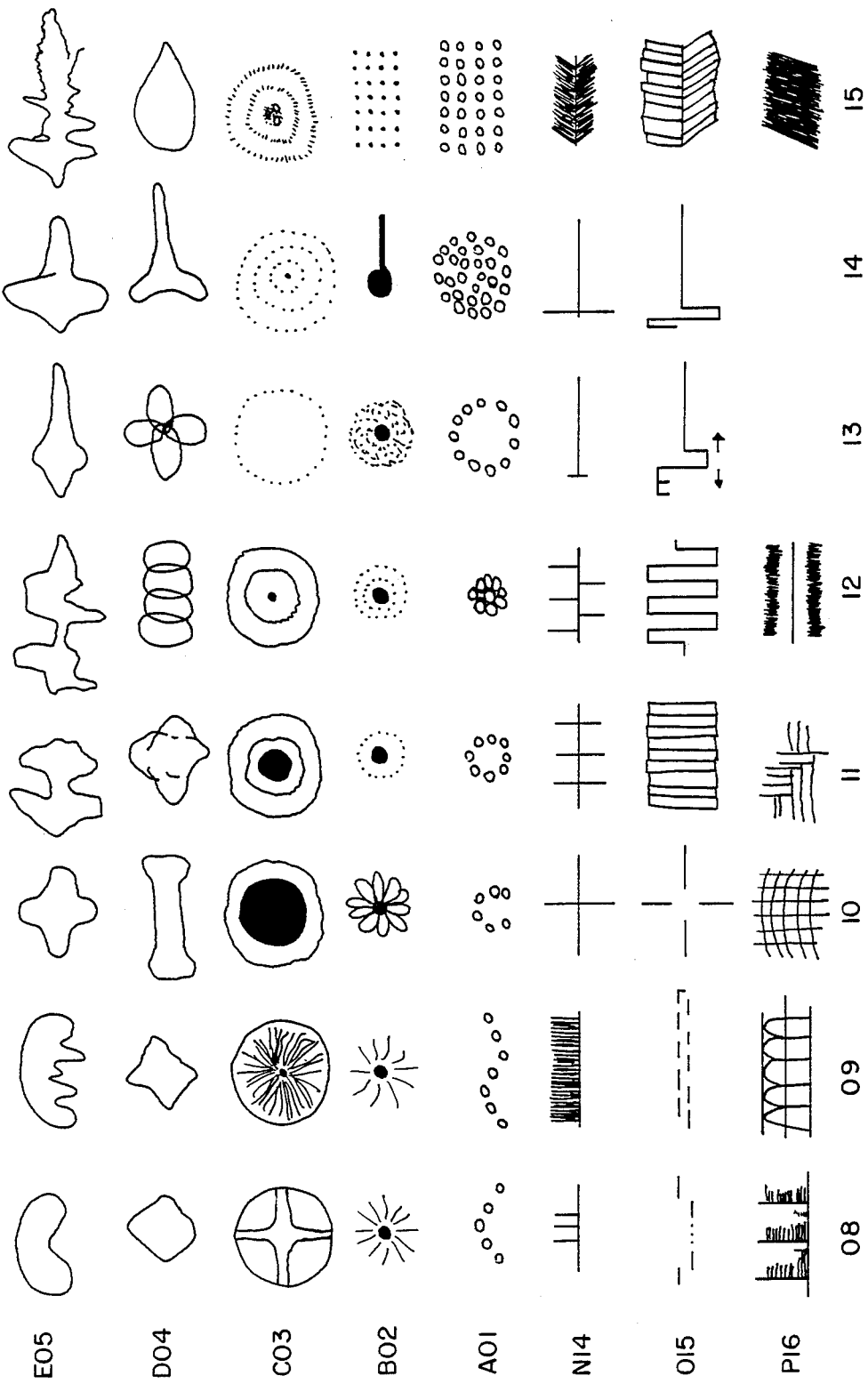
Figure 3:
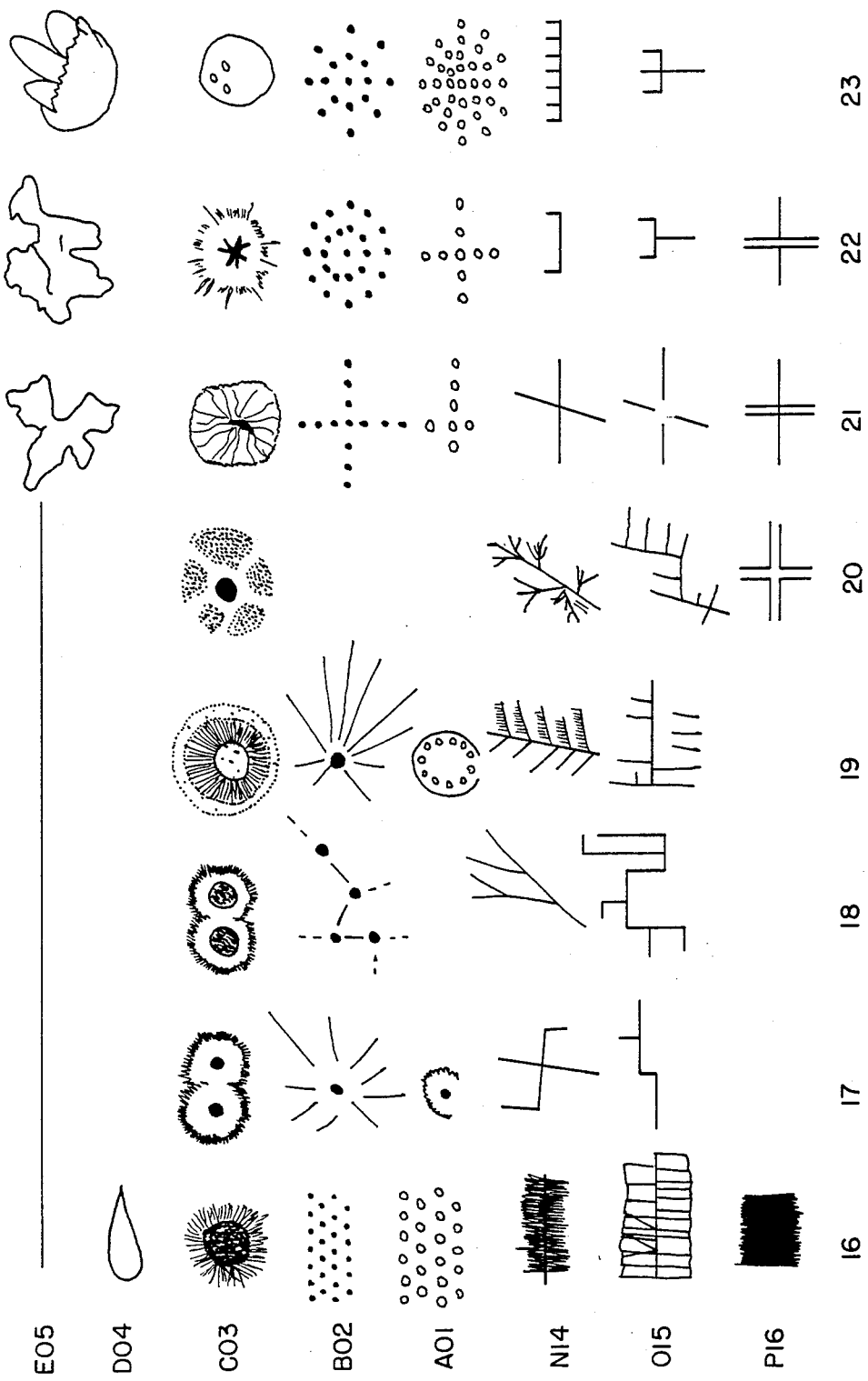

| | Figurative representation: |
|---|---|
| (1) A 01 | circular forms |
| (2) 0-17, 19 21-26 | with infilled inner surface, their lines, accumulations, ordered and unordered grid formation, as shown in FIGS. 1-4, |
| (1) B-02 | circular forms with |
| (2) 01-19 21-26 | filled inner area, their heap-shaped, regular or irregular grid formations, and also their radial, centrifugal, free or interlaced additions and ring formations, as shown in FIGS. 1-4, |
| (1) C 03 | circular forms with |
| (2) 01-27 | denser, dot-shaped, areal, heap-shaped, filled inner area or with raidal or crossing, or centrifugal individual-, mixed-inner forms, as shown in FIG. 1-4, |
| (1) D 04 | oval and geometric forms |
| (2) 01-16 | with superimposed contour, as shown in FIGS. 1-3, |
| (1) E 05 | oval extension forms with |
| (2) 01-15, 21-27 | branches identations, radial or fanning additions, as shown in FIGS. 1-4, |
| (1) F 06 | round, elongated, extended |
| (2) 01-16, 18-21 | or branched forms with pointed ends and empty inner area, as shown in FIGS. 5-8, |
| (1) G 07 | round, elongated, extended |
| (2) 01-16, 18 21-22 24-26 | or branched forms with round ends and empty inner areas, as shown in FIGS. 5-8, |
| (1) H 08 | rows, fans, branches |
| (2) 01-17, [20]21-27 | and geometric grid formations from small, pressed circles, as shown in FIGS. 5-8, |
| (1) I 09 | rows of small, empty, |

Figure 10:
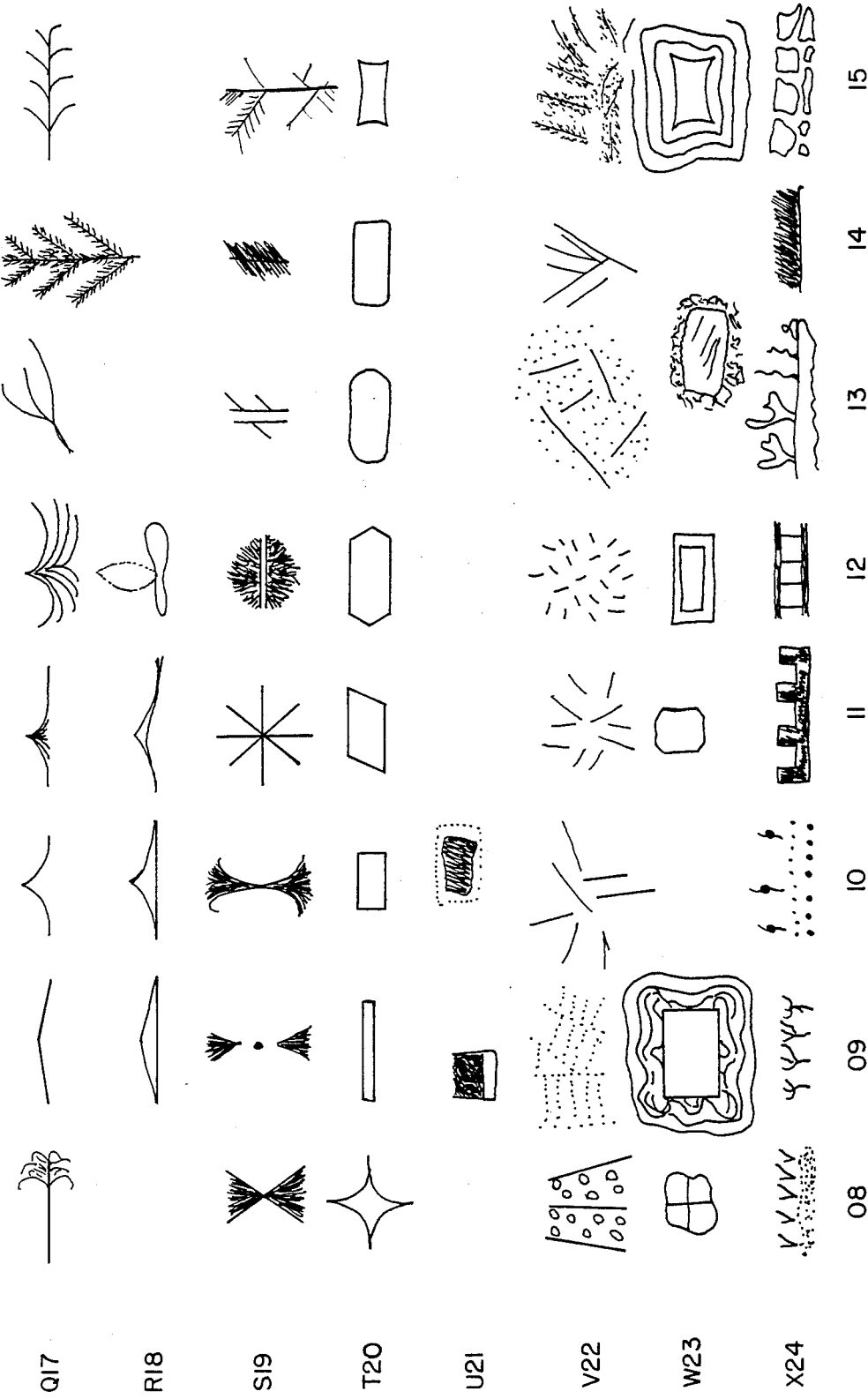
Figure 11:
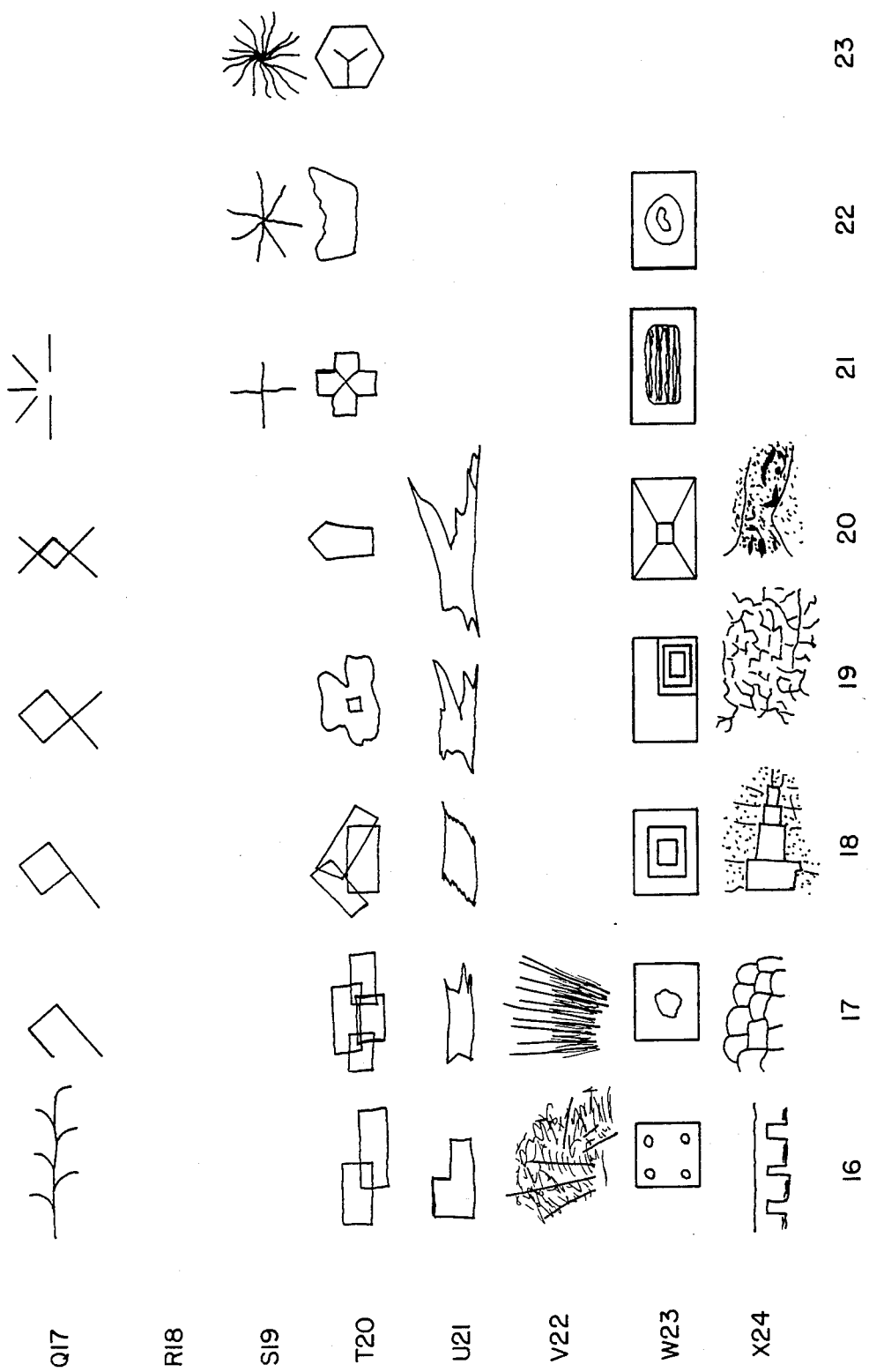

| | -continued |
|---|---|
| | Figurative representation: |
| (2) 01-16 [19] 18-21 [21-22] [0-16 18-21] | pressed circles with branches, accumulations, of small, filled circles, as shown in FIGS. 5-8, |
| (1) K [11]10 | irregular, divided, |
| (2) 01-23,25,27 | negative circles in geometrically ordered or unordered areas, free or filled with geometric forms, such as their positive representations, as shown in FIGS. 5-8, |
| (1) L 12 | sinusoidal, simple, joined, |
| (2) 01-21 24-27 | crossing, heap-shaped forms, forming geometric grids, as shown in FIGS. 5-8, |
| (1) M 13 | bent lines with |
| (2) 01-23,26 | crossings, comb- and ladder-shaped forms, forming geometric grids, as shown in FIGS. 5-8, |
| (1) N 14 | simple line forms with |
| (2) 01-25 | branches on one and both sides, alternating stem or opposite stem, as shown in FIGS. 1-4, |
| (1) 0 15 | simple and bent |
| (2) 01-[25]23 | line forms with branches on one and both sides, alternating stem or opposite stem, as shown in FIGS. 1-4, |
| (1) P 16 | double or multiple, |
| (2) 01-12 15-16 20-22 | mostly parallel, crossing line forms, as shown in FIGS. 1-3, |
| (1) Q 17 | angular line forms with |
| (2) 01-21 | cluster-like branches and/or with arc formations in the angle shanks, and also their crossings, as shown in FIGS. 9-11, |
| (1) R 18 | triangular forms, as shown in FIGS. 9-10, |
| (2) 01-7, 9-12 | |
| (1) S 19 | simple crossing forms, |
| (2) 01-15 21-23, 25 | and their bundling to geometric forms, as shown in FIGS. 9-12, |
| (1) T 20 | four-cornered and multi-cornered |
| (2) 01-23,25,27 | forms and their agglomerates, as shown in FIGS. 9-12, |
| (1) U 21 | four-cornered and multi-cornered |
| (2) 01-4, 9-10, | forms with irregular |

Figure 13:
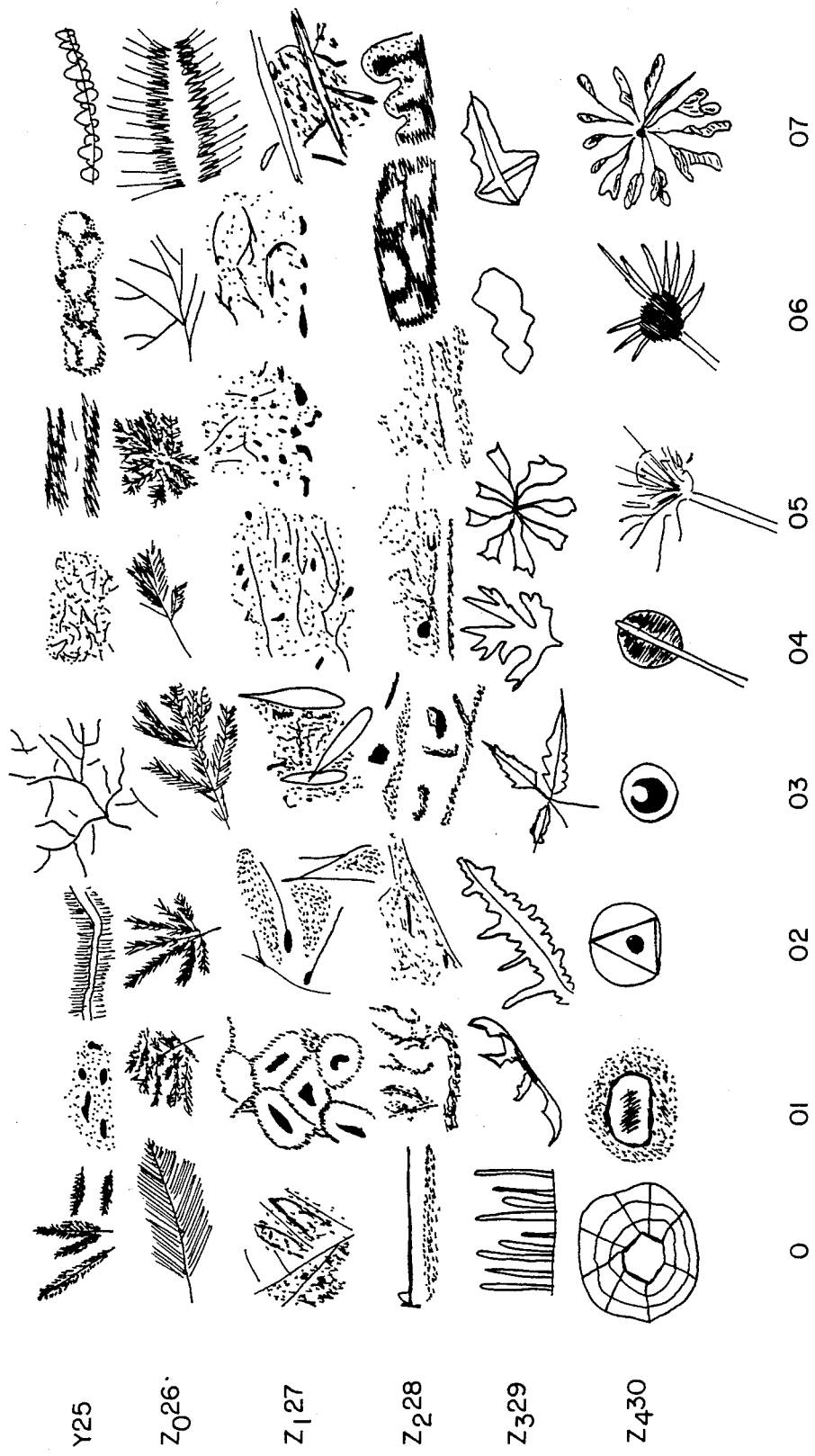
FIGS. 13–15 schematically illustrate mother and daughter forms for Y 25–$Z_4$ 30 representations.
Figure 14:
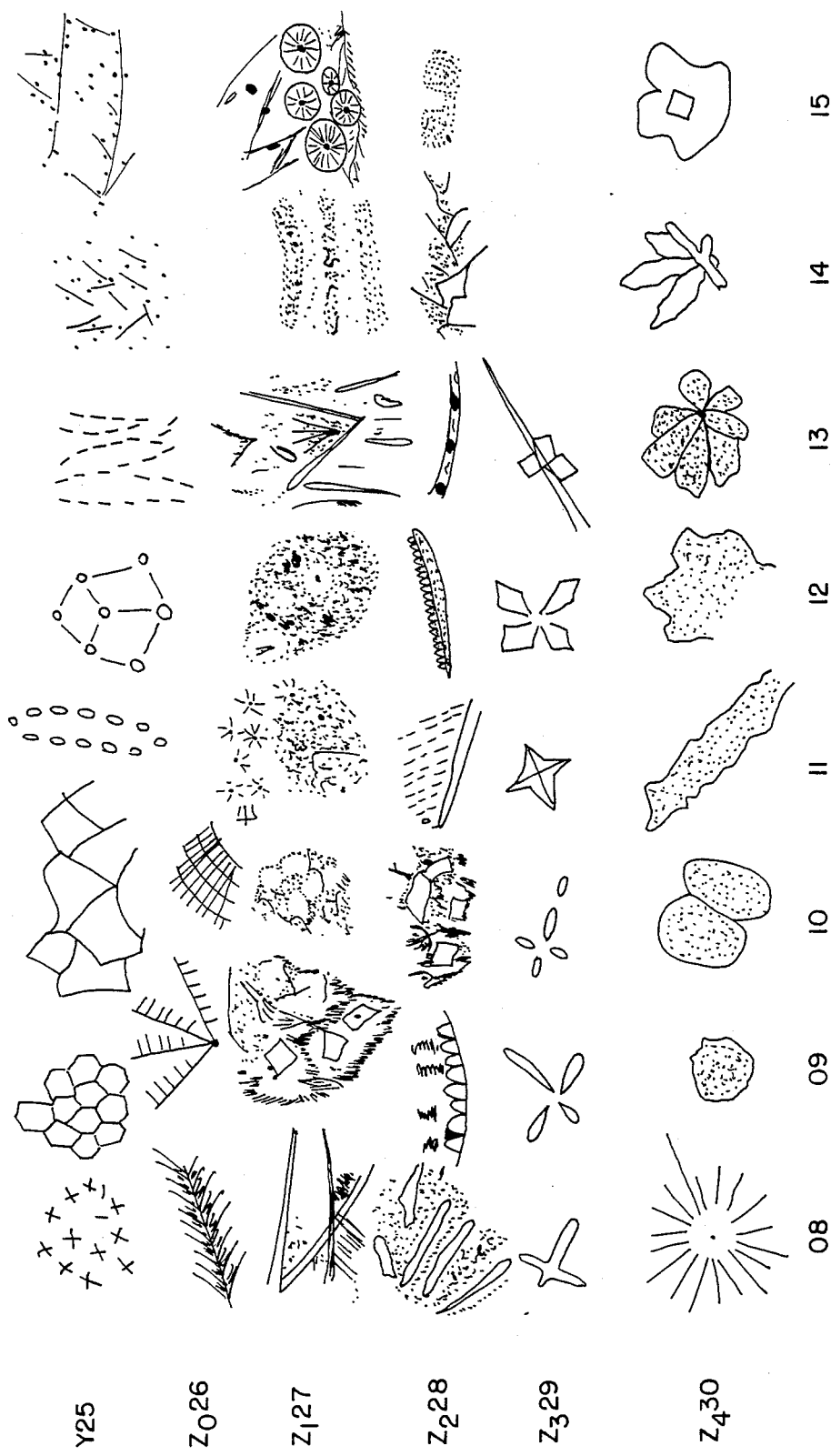
Figure 15:
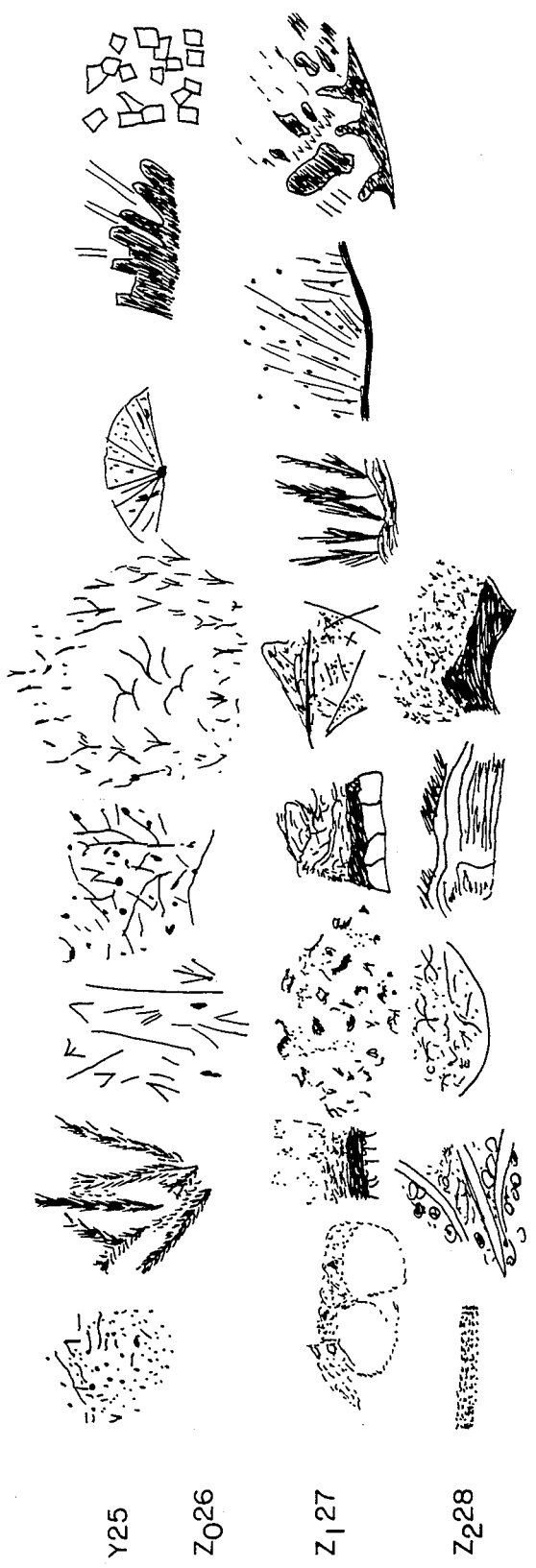
Figure 20:
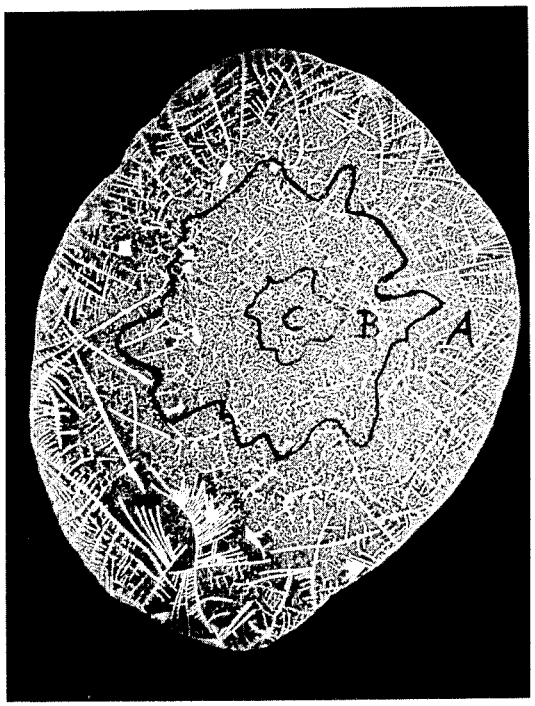
FIG. 20 is a photograph of a 12.5 times microscopic enlargement of crystals showing the regions over-all.
Figure 21:
FIG. 21 is a photograph of a 25 times microscopic enlargement of crystals showing the individual form and texture of regions (A), (B) and (C).
Figure 22:
FIG. 22 is a photograph of a 65 times microscopic enlargement showing dendrite form.
Figure 23:
FIG. 23 is a photograph of a 160 times microscopic enlargement showing the geometric basic form.
Figure 24:
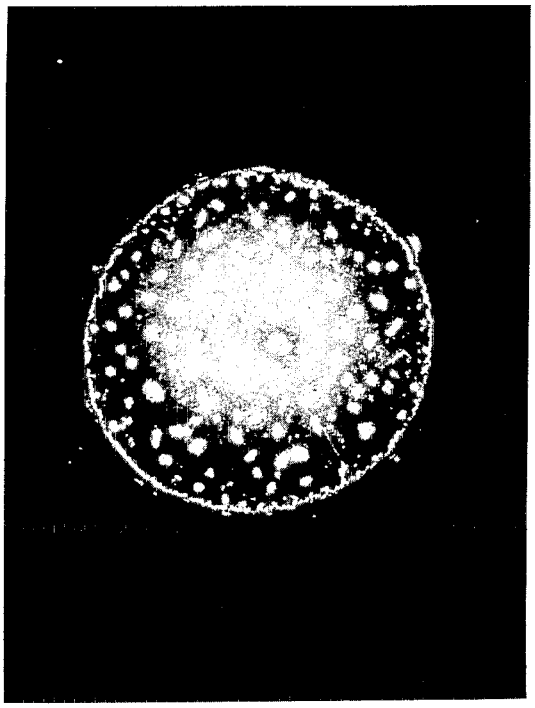
FIGS. 24–27 are photographs which contain the crystal structures and forms of the blood of a sick person.
Figure 25:
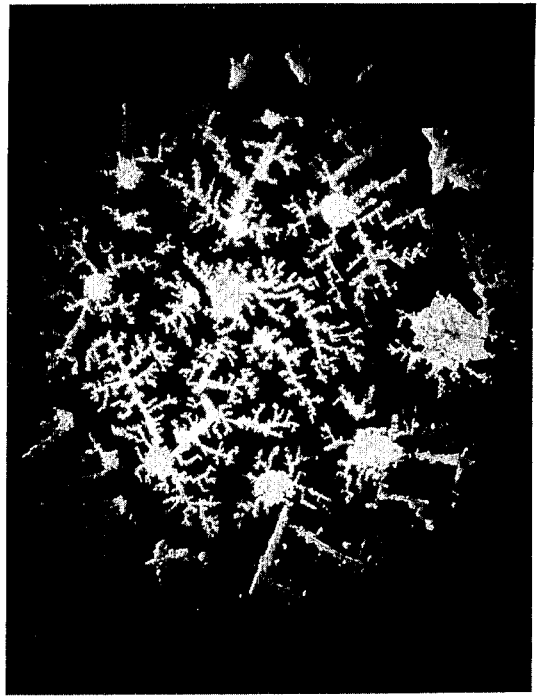
Figure 26:
Figure 27:

| | Figurative representation: |
|---|---|
| 16-20 | partially deformed contours, as shown in FIGS. 9-11, |
| (1) V 22 | extended line |
| (2) 01-17 | forms with free or crossing arrangement to shorter extended forms or to punctiform forms, as shown in FIGS. 9-11, |
| (1) W 23 | four-cornered forms with |
| (2) 01-9 | geometric additions |
| 11-13,15-22 | on the outer sides and geometric incorporations into the inner surfaces, as shown in FIGS. 9-11, |
| (1) X 24 | band forms of |
| (2) 01-20 | elements lying transversely or angularly to the direction of course of the band, and their connections or of punctiform rows or of periodic, free or geometric forms, as shown in FIGS. 9-11, | and the forms according to the coordinates:
Y 25 01-23 as shown in FIGS. 13-15
$Z_0$ 26 01-10 as shown in FIGS. 13-14
$Z_1$ 27 01-23 as shown in FIGS. 13-15
$Z_2$ 28 01-20 as shown in FIGS. 13-15
$Z_3$ 29 01-13, 16, 17 as shown in FIGS. 13-15
$Z_4$ 30 01-15 as shown in FIGS. 13-14.

6. Method according to claim 5, wherein the crystal textures and crystal forms have geometric and morphological figures as coordinates, which are derived from the mother forms and from the daughter forms through addition, connection, superimposition, whereby the expression in front of a bracket represents the superordinate, figure-forming form, and the expression in a bracket represents a subordinate partial form, with the coordinates:

| | |
|---|---|
| $Z_1$27-15: (C03-09) + (N14-18) + (V22-06) | , as shown in FIG. 16 |
| $Z_1$ 27-16: n(D04-00) + (Q17-06 + A01-24) | , as shown in FIG. 17 |
| $Z_1$ 27-09: (K11-03) (T20-00/W23-00/ W23-17/C03-23/C03-00) Y25-(01-07) | , as shown in FIG. 18 |
| $Z_026$-(01-07) $Z_127$-(01-07) $Z_228$-(01-07) $Z_329$-(01-07) $Z_430$-(01-07) | , as shown in FIG. 13 |
| Y25-(08-15) $Z_026$-(08-10) $Z_127$-(08-15) $Z_228$-(08-15) $Z_329$-(08-[03]13) $Z_430$-(08-15) | , as shown in FIG. 14 |
| Y25-(16-23) $Z_127$-(16-23) $Z_228$-(16-20) $Z_329$-(16-17)— | , as shown in FIG. 15 |

7. Method according to claim 1 wherein the crystallization to textures and forms in step 8 in the regions (A), (B), (C) takes place in reciprocal representation with respect to nature and within these regions in the concentric circles as topology of the organs and organ zones in a defined sequence from the outside inwards in radial direction with the following allocation:
Endodermal region: outer circle: head cavities, teeth, pharynx/tonsils, lymph, lung, stomach/duodenum, small intestine, large intestine, rectum, liver, bladder, uterus/prostate,
Mesodermal region: middle circle: pancreas, connective tissue, musculature, bones, joints, kidneys, heart,
Ectodermal region: inner circle: endocrine system, skin, central and peripheral nervous system (CNS, PNS)
and the allocation through analogy comparisons takes place with crystal textures and crystal forms, produced according to method steps (1) to (8), from clinically established clinical pictures.

8. Method according to claim 1 where in step (1) the ratio of blood or urine to water is 1:2.7 to 3.2.

9. Method of claim 1 where in step (2) heating at a constant rate is conducted for a period of about 65 minutes.

10. Method of claim 1 where in step (8) the drops have a diameter of 8 mm.

11. Method of claim 2 wherein a quantity of 7 to 10 ml. of human or animal blood or urine is used.

* * * * *

UNITED STATES PATENT AND TRADEMARK OFFICE
CERTIFICATE OF CORRECTION

PATENT NO. : 4,847,206
DATED : July 11, 1989
INVENTOR(S) : Ullrich Heinz

It is certified that error appears in the above-identified patent and that said Letters Patent is hereby corrected as shown below:

Column 1, line 29: "1:27" should read as --1:2.7--

Column 3, line 27: "method" should read as --mother--

Column 7, line 39: "15-20" should read as --0 15-20 --

Column 7, line 43: Add "27" to the left of "Region (A):"

Column 13, line 67, Claim 5: Delete "[20]"

Column 14, line 34, Claim 5: Delete [19]"

Column 14, line 35, Claim 5: Delete "[21-22]"

Column 14, line 36, Claim 5: Delete "[0-16 18-21]"

Column 14, line 37, Claim 5: Delete "[11]"

Column 14, line 53, Claim 5: Delete "[25]"

Signed and Sealed this

Twenty-fourth Day of July, 1990

Attest:

HARRY F. MANBECK, JR.

Attesting Officer

Commissioner of Patents and Trademarks